US009833507B2

(12) United States Patent
Iyer et al.

(10) Patent No.: US 9,833,507 B2
(45) Date of Patent: Dec. 5, 2017

(54) PORCINE PARVOVIRUS 5A, METHODS OF USE AND VACCINE

(71) Applicant: Boehringer Ingelheim Vetmedica, Inc., St. Joseph, MO (US)

(72) Inventors: Arun V. Iyer, Ames, IA (US); Dianna M. Murphy Jordan, Ames, IA (US); Abby Rae Patterson, Story City, IA (US); Michael B. Roof, Ames, IA (US); Eric Martin Vaughn, Ames, IA (US); Joseph Gilbert Victoria, Ames, IA (US); Callie Ann Visek, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 255 days.

(21) Appl. No.: 14/713,700

(22) Filed: May 15, 2015

(65) Prior Publication Data

US 2015/0246113 A1 Sep. 3, 2015

Related U.S. Application Data

(62) Division of application No. 13/796,621, filed on Mar. 12, 2013, now abandoned.

(Continued)

(51) Int. Cl.
*A61K 39/23* (2006.01)
*G01N 33/68* (2006.01)

(Continued)

(52) U.S. Cl.
CPC ............ *A61K 39/23* (2013.01); *C07K 14/005* (2013.01); *C12N 7/00* (2013.01); *G01N 33/6893* (2013.01);

(Continued)

(58) Field of Classification Search
None
See application file for complete search history.

(56) References Cited

U.S. PATENT DOCUMENTS

| | | | |
|---|---|---|---|
| 6,228,846 | B1 | 5/2001 | Audonnet et al. |
| 2014/0170180 | A1 | 6/2014 | Iyer et al. |

(Continued)

FOREIGN PATENT DOCUMENTS

| | | | |
|---|---|---|---|
| EP | 0117767 | A1 | 9/1984 |
| WO | 9803199 | A1 | 1/1998 |

(Continued)

OTHER PUBLICATIONS

Mengeling et al., "The effect of porcine parvovirus and porcine reproductive and respiratory syndrome virus on porcine reproductive performance," Animal Reproduction Science 60-61: 199-210 (2000).*

(Continued)

*Primary Examiner* — Janet L Andres
*Assistant Examiner* — M. Franco Salvoza
(74) *Attorney, Agent, or Firm* — Marc Began; Joyce L. Morrison

(57) ABSTRACT

The present invention provides novel nucleotides sequences, protein sequences, immunogenic compositions, vaccines, and methods that relate to making and using new porcine parvovirus 5A (PPV5A) that infects, inter alia, domestic swine. The compositions and methods provide for the detection of infections by said new virus, monitoring genetic changes in the viral sequences in wild and domestic animals and herds, and making and using novel vaccines for protecting animals from infection by the virus.

9 Claims, 9 Drawing Sheets

Phylogenetic analysis of VP1/CAP region of PPV5A

Related U.S. Application Data

(60) Provisional application No. 61/738,110, filed on Dec. 17, 2012.

(51) Int. Cl.
*C07K 14/005* (2006.01)
*C12N 7/00* (2006.01)
*A61K 39/00* (2006.01)

(52) U.S. Cl.
CPC ................ *A61K 2039/5252* (2013.01); *A61K 2039/5254* (2013.01); *A61K 2039/552* (2013.01); *C12N 2750/14021* (2013.01); *C12N 2750/14022* (2013.01); *C12N 2750/14034* (2013.01)

(56) References Cited

U.S. PATENT DOCUMENTS

| | | | |
|---|---|---|---|
| 2014/0234354 | A1 | 8/2014 | Iyer et al. |
| 2015/0283230 | A1 | 10/2015 | Iyer et al. |

FOREIGN PATENT DOCUMENTS

| | | | |
|---|---|---|---|
| WO | 9811244 A2 | 3/1998 | |
| WO | 02068698 A2 | 9/2002 | |
| WO | 2011063320 A2 | 5/2011 | |
| WO | 2014099669 A1 | 6/2014 | |
| WO | 2014127084 A1 | 8/2014 | |

OTHER PUBLICATIONS

Martinez et al., "Production of porcine parvovirus empty capsids with high immunogenic activity". Vaccine, vol. 10, No. 10, 1992, pp. 684-690.
Canuti et al., "Two Novel Parvoviruses in Frugivorous New and Old World Bats". PLOS One, vol. 6, No. 12, e29140, Dec. 2011, pp. 1-9.
Cheung et al., "Identification and molecular cloning of a novel porcine parvovirus". Archives of Virology, vol. 155, 2010, pp. 801-806.
Cui et al., "Genome Sequence of Chinese Porcine Parvovirus Strain PPV2010". Journal of Virology, vol. 86, No. 4, 2012, p. 2379.
Database UniProt Accession No. K4K2G7, Jan. 9, 2013, Retrieved from EBI accession No. UNIPROT: K4K2G7, pp. 1-3.
Database UniProt Accession No. K4K4H5, Jan. 9, 2013, Retrieved from EBI accession No. UNIPROT: K4K4H5, pp. 1-3.
Duffy et al., "Rates of evolutionary change in viruses: patterns and determinants". Nature Reviews Genetics, vol. 9, 2008, pp. 267-276.
GenBank Accession No. EV964070.2, Gorodkin et al., "Porcine transcriptome analysis based on 97 non-normalized cDNA libraries and assembly of 1,021,891 expressed sequence tags". The Royal Veterinary and Bioinformatics, (IBHV) and Center for Bioinformatics, Aug. 2007, 1 page.
GenBank Accession No. EV966948.2, Gorodkin et al., "Porcine transcriptome analysis based on 97 non-normalized cDNA libraries and assembly of 1,021,891 expressed sequence tags". The Royal Veterinary and Bioinformatics, (IBHV) and Center for Bioinformatics, Aug. 2007, 1 page.
GenBank Accession No. JQ037754.1, Canuti et al., "Two Novel Parvoviruses in Frugivorous New and Old World Bats". Laboratory of Experimental Virology, Department of Medical Microbiology, Academic Medical Centre (AMC), Dec. 2011, pp. 1-3. [Accessed at http://www.ncbi.nlm.nih.gov/nuccore/jq037754 on May 16, 2014].
GenBank Accession No. JX896318, Xiao et al., "Identification of a new porcine parvovirus: an evidence for the coexistence of different intermediates during the evolution of parvovirus". College of Veterinary Medicine, Iowa State University, Department of Veterinary Diagnostic and Production Animal Medicine, Oct. 2012, pp. 1-4.
GenBank Accession No. JX896321.1, Xiao et al., "Porcine parvovirus 5 isolate IA469 clone 1, complete genome". College of Veterinary Medicine, Iowa State University, Department of Veterinary Diagnostic and Production Animal Medicine, 2013, pp. 1-3.
Gorodkin et al., "Porcine transcriptome analysis based on 97 non-normalized cDNA libraries and assembly of 1,021,891 expressed sequence tags". Genome Biology, vol. 8, No. 4, Apr. 2007, pp. R45.1-R45.16.
Huang et al., "Detection of a novel porcine parvovirus, PPV4, in chinese swine herds". Virology Journal, vol. 7, No. 1, 333, Nov. 2010, pp. 1-4.
International Search Report and Written Opinion for PCT/US2013/075059 dated May 13, 2014.
Józwik et al., "Vaccination against porcine parvovirus protects against disease, but does not prevent infection and virus shedding after challenge infection with a heterologous virus strain". Journal of General Virology, vol. 90, No. 10, Jun. 2009, pp. 2437-2441.
Lytle et al., "Predicted Inactivation of Viruses of Relevance to Biodefense by Solar Radiation". Journal of Virology, vol. 79, No. 22, Nov. 2005, pp. 14244-14252.
Ma et al., "The immune enhancement of propolis adjuvant on inactivated porcine parvovirus vaccine in guinea pig". Cellular Immunology, vol. 270, 2011, pp. 13-18.
Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.
Wang et al., "Enhancing immune responses to inactivated porcine parvovirus oil emulsion vaccine by co-inoculating porcine transfer factor in mice". Vaccine, vol. 30, 2012, pp. 5246-52520.
Wu et al., "First complete genomic characterization of a porcine parvovirus 5 isolate from China". Archives of Virology, Dec. 2013, pp. 1-4.
Xiao et al., "Characterization of a Novel Porcine Parvovirus Tentatively Designated PPV5". PLOS ONE, vol. 8, No. 6, e65312, Jun. 2013, pp. 1-11.
Xiao et al., "Complete Genome Sequence of a Novel Porcine Parvovirus (PPV) Provisionally Designated PPV5". Genome Announcements, vol. 1, Issue 1, e00021-12, Jan./Feb. 2013, pp. 1-2.
GenBank Accession No. JX896320.1, Xiao et al., "Complete Genome Sequence of a Novel Porcine Parvovirus (PPV) Provisionally Designated PPV5". Genome Announcement, vol. 1, No. 1, E00021-12, 2012, pp. 1-3.

* cited by examiner

FIG.1

PPV5A DNA Sequence

PPV5A_Reference:

```
gene            87..1967
                /label="Predicted replicase"
gene            1975..2844
                /label="Predicted gene of unknown function /
ORF3"
gene            2845..5547
                /label="Predicted Capsid"
Sequence:
TATTTGCAGGCTTTTCCCTGATATTGGGAAGATTCCTGGGGTGACTCCTGAGCGGTATATTTAT
GCTGTAAACGTGAGTACCCGTAATGGGCAAAAGTGGCCGAAAGTTGGGACCGAGGGGCCATTGG
CTGCAGGTGTCTTACAGGGGGAGGCCCTTTTCCGTGAGACCCTTAAAGAGGTCCGGAAGGTGTG
CCGGCTGCCGCAAGACCCCCCATCTTTTCTTTCAATTGGAGAAAGTTGATTCCAAAGGGGGTCT
TCACCTTCATTTTTGTATTAGTGTTGCTGCTGGCACTCCTAGAGATGTGTCTTCGATGTTTAAA
GCCATTGAGCGTCGAGTTTCCTTTTACTACTTTGGTGTAGAGGGCTTGACTTTTTTTACTCCTC
ATAAAAATAAGCATGGGGCTTGGAAGAGTAATGATGAGGGCTTTATTGTGAATTATCTTCTTAA
AAAATTGCCTTTGTCTGAGTGTGTGTATGCGTGGACTAATATGGATGGGGTGATTGGCGATGCC
TGTCTGAATGAAGATAAGCGCAGGGAATTGTTGTCTGAGCGTCAAGATCAGGGAGTCATTAAAG
AGCTCACTGCTCCTACTTTTAAAGCTGCTACGGGTGATAAAATGTTGAGTGTGGTGGATTGGAT
GTGTGATAATGATGTGACTACGGAGCGCCGATGGGAGGAAATATCGGCTGCGTCCCTGTACTCT
TTCCTTGCTACCCCAGCTGGCACTCATTTGGCTAAACAGTGTCTTAGAGCTGCGAATCAGCGTA
TTGTGAGCACTAAAACCTCTTGGTTGAGTCTCTGTAAATTTGCCAGTGAAAAGGAGCTTCGTGC
TTTTCAAAATGGGGATCCTGAGTTGTCTTCAGACAACAATAGGATCTATTACTTATTTGCTATG
AATAATTACTGCCCTGATATGGCCAGTATGATTTTCTTTTGGTGGTCTATGCGCCAAACGGGTA
AGAGAAACAGTATTTGGCTGTTTGGACCTGCTACAACCGGTAAAACCAATTTAGCAAGTGCTAT
TGCACATACTGCTGCCAGTTATGGGTGTGTTAACTGGAATAACGCAAATTTCCCGTTTCAAGAC
ATTGTGAATGTGCAACTGGGTTGGTGGGAGGAAGGAAAGATGACAGAGGATGTGGTTGAATGTG
CTAAGGCATTGCTAGGGGGAAGTAATGTAAGAGTTGACCGCAAATGTATGCAATCTGCGGAAGT
GCAATCTCCTCCTTTTATTATCACATCCAATACGGATATGTGCCTTGTTTCTCAAGGCAGTTAC
ATCAGTTTTGAGCACCAGCAGCCTCTCCAGGATAGAATGATTAAATTTGAGTTTAACCATGTTC
TTCCTGGCAATTTCGGCCTCATTTCTGAAGATGAAGTTGTGGCCTTCTTCAGAAATGGTGCTTA
TAATGTGTTGAAGCATGCGTACATGAGAAAGGCCCAGCTTTTTGCTCTCGGTCCAGCTTCCTTG
CCATATAAGCCCCCTACGGGTGAATTAGTGTGTATAGACCAAGCTAAGTCTCCTTCTCCCTCTG
CTTCTCGCCGCAGTGTGAGAAATTGGATGACGTGTCCCCCTGATCCTGTCCAGGACGATCCCGC
TGAACTGGACGAGTATTTTCCTCCAGATACTCCTCCAGAGGATTGTCCTTGTCCTATTTCTCCT
GTGAGGGAGTCTTGTCCCTCGCCAGGGCCTTGCCCTACCCCTCCTCGCAAAAAACAACGGAAGA
GCAAGCATTGCTCCTTGTCTGTCTCTGCGGGTAAAGTTCCTGTGGTGGTTGTGGGTGATTCTGA
CTCAGTCCCCCCCGAAGAAAAAGAAAAAGAGGAAGTTTCCGTGGGGGAATCCCAGGATCCACAA
CTGTACTGGGACCTAACTCTCAGTCAATCCGACGTTCCTGTGCCTGAAGACGAGAGTACCCAGT
TTCCTGACGACGCTGTGGACGCTTCTGATCTCATTGCTGAACAGTAGTTAAGGTATGAGCCGTT
CTACTCAAAGAGATCTTTGGTCTTTGTTAAGGGAGAGACTTGAAAGGTATAAGGATCGAGTTAA
ATATTATGGTATTTTGGTGCCAGAACGTCCTTCTACCTTAGCATCTTATTTTAGTAAAGACCCA
CCTCCAGATCCTCCAACTGTTAAATTTGATAAACCCTATCAGGATGTAGATAGATTCTGGTTTC
```

FIG.1 (Cont.)

PPV5A DNA Sequence

CAACAGACGATTATACTGACTGGTATGTCTGGCATGGAGAGGACAGACCTCCTAGATTTACCGA
GCATTCCGGTGTTCAGGGTTTTAAAACTAGGTGTGAGGGGGGGCTTCCTTTAATGCCCAGTGAT
CCCAAATTTTGCCCCATACAAAATTTTTGGGATCAGTTCGCTAATTTTGATGAGGGGTCTCCGT
CCACCCAGATCGGTGAGAGTGTTTCATGGAGTGATCATTTTGGAAGTCCCGATCCCTCTCATCA
TCAGGAGGTGAGGGATGCTGATGAAGTTACTTCCGAGCGGCAGCAATATAAAAATAGGATTGTC
ACCTTACTAAGAAAAGTTTATTGGGCTAAGCAGTGGTCTGGGAAATTACAAATTAATGTTCCTT
CCCTCGAAAGCCTTTATGAGCAGATCCCCTATATGCTAGCCTATATGGACGCCGATAATTGGCG
TCAGAATTTGTTAGCTGCTAAAACTCTGCGAACCACTTTGGAAGCATTTTCCTGTGTTCCAGAT
CCTTCCACGTGCGATGTCACAATCTCCACACCCCTATCTGGTGAAACGGATCCCGCCTCTTTTG
CAAAATACTTATGTTCCCTTGTATGCAACAGGTCTCAAGAAAAAGAACAGGCGCAGACGCCTTC
TTTGTCTCCATCTAAGCAAAAAGGGCAGATGTCAAGTCCTGATTCTGCATCGATCTCCCAACCT
CCCCCTGAAAGTCACAAGGATAGACTGCTTCCTAAAACTGATCCCCTTCAGGAAGCAGGGCCCC
TTCCCGCTCCCCCTACAGCTCAGAAGCCTATTATCTCTAAGGGTGCAGGCGGTGGAGGGTCGTC
TGGCTTCATAATCCCTCCAAAACCTCCTAGCCCCGATCATACTAAAGATCCCCCCCCTCCTCCT
CCTCCCTCTCCAATTCCTCCTCCTACATCTGCGCCTGACGCAGAGGAGCACGAGCTAGAGCGTG
CTAAGCAGGAGAAACAAGAGGAAGATGAGCTCATTGAAAGAATCAAATCAGGAGAAGGAGAAGG
AGAACGAGGAGGCTTCGTCTTGCCTTCTCACCACTACACTGGTCCTAGAAATCCTGTCCCAGCT
GGCAAGCCTGCTGACCCCGTTGATGAATCTTCTGCGAGACATGACATCAGGTATGGGCAACGTC
TTAAACATGGAGACTGGCCATACCTGTGGGGGAAGGACTTGGATAATGCTCAGCGAGATGAGAT
TATCAAAGCTCTTCATAGTCATGTCAAAGTGGGAACCCAATTGGCAGGGAATATAGTGAGGAGT
ATCTGGAAGGCTAAGGAGCTCTTAACAGAACCTGTGTATGAGCTGTTAAAGTCTATTCTCCCTC
CTTCAGATTTATCTAAAGTTCCTCTTCCTCATTCCCAACAGACAGACAGAACAGAAGATCCAGA
AACTCCAGGGGAGACTAGAGGAACTGGATCAGACAGTCCTCGATCTCCTCGGCCTTCTGGATCA
ACTGAAGACGGGGGAGGTCCTTCTTCCGAGTCCAGATTACCTGGGAGTAAAGTTCCAGTAGACC
CATCTGCCACCACGTCTGAAGCAAAGAGGCAGAGGACTGAGGAGGGGATGGACATATCTTCATG
CGGTCCAGGGGGGATTTCTGCTTCTGGGGCTGCTTCAAATAACTCTGGTCTTGCTTGTGGGGGT
GGGGGGGGTACTAATTTAGGGACAGAATCTCTTGTATCCGGCTGTCAGTTTGGTAAAAACTCTG
TGATCACTTCATCTTTTAGACGATGTCTTATTTCACCCTGGCCTGATAAATACTGTTGTTCTTC
TGCTCACGATCTTATTCCCGGAGTGGTCTACGAGACCCCTTGGTGCTATTATGATCTGAACGTC
ATCTCAAGCTACATTTTTTCTCCTTCTGCTTGGCAGAGGCTTTTGGAGGATTATGATGCCTTTC
GACCTAAATCCCTTAAAGTTACCATCCAGTCTTTAGTTTTAAAGATGTCTGTCAAGGTGCAGAA
AAAACAAACTACAGTTCAGGATTCCCAGTCAGCCACTATTGCTATCTTTGAGGATAAAGACTAT
GACTACCCCTATGTGATGGGAGGGGGTCAAAAAACAGTTCCGGGTCACTTGCCCGGTCAACCTT
ATAATCTTCCCAAGTATTCTTACAGAACCCTTGGTTCAGTCAAAGAAAGTAATAGGGCCAGTAT
GGGCGGTTCAGGGTACACTTTCAAATCCAATCAAGATACGGAATTGTTCCTGCTTGAAACACAT
GATGCCACTCTTATTCGAGGCGGGGGTACTTTTGAGCAGTACTATGAATTTCCAAACGATCTTC
CTTTCGAAAATTTGACTCAGTATCCTTGGGATATCCGCCGTCAGGATAACCCCCTCTATCAGCA
GAGGATCACTGTCATGTCAGGTTCTGACAGAGATACGGTAGGCATTCTAGATGGAGATTTTTAC
TCTCCTTTTCGGTTCAAAGGACATGATAGACCCGCCATGTGGCTGCCAGGACAGAGGTTGATTC
AGGGCAAATTCATAGATACGCACCCAATACCCAATACAGGGAGGAGTGGGGTTCATCCTAATGA
TTTTCACACAAGGGGCGATGGTCATGGTGACACCCATAGAACACATGAAGAGAGGATCTACAGT
CTAGATACAGGTCTTGCTGCTATGCCACGTGCCGCTCATAGACCCACCCTTCAGCCCGGACCTA

FIG.1 (Cont.)

GGACTCTGTCTCATGCCGTACGCAGACCCGATGGTTCCACCGTGGTCACGGCTAATGCGTGTGC
TTACGCTTACACCCAGGAGAATCCTCATCAGGAACCCTGGAGTGATCTCAATGTCAGACATACC
ATGTATAGGTTAGCCTATCAACGTCAAAAAGGTTTTCAGCAACCCGGGGACCCTCTTCATATTC

GAACCCATGCTTGTTATGGGGACGGGGATGTTACCATTCCAAAAGAAGAGTCCTTATGGCCTAC
TGTTCTGGGTAGTTGCACAGAAAAGTCCCCTGCCTGTTTAGAGTCCCAGATTTGGTGTAAAACA
CCAAATGTGGACATGGTCTATGGAGAACACACACCCCCCTCTTGCTTTATGGGGTATGCATGCTC
CCCCACCCCATGTATTTCTCAGGATGCTTGCTCAAGAGGGTCCTCCTAATGTCAGTACTTGCAG
ACCGGCTCAATCTGGTCAGACCTTCATCAATCAATATGGTCAGTTTCTCCTCTGTTTTACCATG
GTATGGGAAGTTAAGCCTAGACCCAAGTCCATCAAGCAGTGGAATCCACGTCCGCCCATCAGCA
TTCCTGTTGGTCAGTCTGGTCCTGCTTTCATTCTCGATCAAGATGGCTACTACCGTCTCCCAGA
ACATGTCTGGTCTGCCAGGGAACGTATCCGCAGCAAACGCTAGTGCCCCCAGCAATACACTTAC
TACAGTATTGATGTGTCAGGCATTCTGGTTGATTGTTTTATTTTGGCTCCGCCTACTGTATGGC
CCATGTAAACGCATCTATTATGAAAATAAAATACGTCAATTGCTGATGTAATTCGTGTTGTAAT
TCTTGTTTTGAAAAGCGCATATTTTCTTGCCGGTCTGAGTAACACCACCTATGACATCATATAA
ATTTGATTACGTAACTTCCTCTTTTTACTTCCGTCTTTTTTTGATTACGCAATATACACAATTC
TAGCAGTTAACTATTACACAATATCACAC

FIG. 2

PPV5A REPLICASE PROTEIN SEQUENCE

MGKSGRKLGPRGHWLQVSYRGRPFSVRPLKRSGRCAGCRKTPHLFFQLEKVDSKGGLHLHFCIS
VAAGTPRDVSSMFKAIERRVSFYYFGVEGLTFFTPHKNKHGAWKSNDEGFIVNYLLKKLPLSEC
VYAWTNMDGVIGDACLNEDKRRELLSERQDQGVIKELTAPTFKAATGDKMLSVVDWMCDNDVTT
ERRWEEISAASLYSFLATPAGTHLAKQCLRAANQRIVSTKTSWLSLCKFASEKELRAFQNGDPE
LSSDNNRIYYLFAMNNYCPDMASMIFFWWSMRQTGKRNSIWLFGPATTGKTNLASAIAHTAASY
GCVNWNNANFPFQDIVNVQLGWWEEGKMTEDVVECAKALLGGSNVRVDRKCMQSAEVQSPPFII
TSNTDMCLVSQGSYISFEHQQPLQDRMIKFEFNHVLPGNFGLISEDEVVAFFRNGAYNVLKHAY
MRKAQLFALGPASLPYKPPTGELVCIDQAKSPSPSASRRSVRNWMTCPPDPVQDDPAELDEYFP
PDTPPEDCPCPISPVRESCPSPGPCPTPPRKKQRKSKHCSLSVSAGKVPVVVVGDSDSVPPEEK
EKEEVSVGESQDPQLYWDLTLSQSDVPVPEDESTQFPDDAVDASDLIAEQ

FIG.3

PPV5A ORF3

MSRSTQRDLWSLLRERLERYKDRVKYYGILVPERPSTLASYFSKDPPPDPPTVKFDKPYQDVDR
FWFPTDDYTDWYVWHGEDRPPRFTEHSGVQGFKTRCEGGLPLMPSDPKFCPIQNFWDQFANFDE
GSPSTQIGESVSWSDHFGSPDPSHHQEVRDADEVTSERQQYKNRIVTLLRKVYWAKQWSGKLQI
NVPSLESLYEQIPYMLAYMDADNWRQNLLAAKTLRTTLEAFSCVPDPSTCDVTISTPLSGETDP
ASFAKYLCSLVCNRSQEKEQAQTPSLSPSKQKGQ

Fig. 4:

PPV5A CAPSID PROTEIN SEQUENCE

MQRINSGEGEGERGGFVLPSHHYTGPRNPVPAGKPADPVDESSARHDIRYGQRLKHGDWPYLWG
KDLDNAQRDEIIKALHSHVKVGTQLAGNIVRSIWKAKELLTEPVYELLKSILPPSDLSKVPLPH
SQQTDRTEDPETPGETRGTGSDSPRSPRPSGSTEDGGGPSSESRLPGSKVPVDPSATTSEAKRQ
RTEEGMDISSCGPGGISASGAASNNSGLACGGGGGTNLGTESLVSGCQFGKNSVITSSFRRCLI
SPWPDKYCCSSAHDLIPGVVYETPWCYYDLNVISSYIFSPSAWQRLLEDYDAFRPKSLKVTIQS
LVLKMSVKVQKKQTTVQDSQSATIAIFEDKDYDYPYVMGGGQKTVPGHLPGQPYNLPKYSYRTL
GSVKESNRASMGGSGYTFKSNQDTELFLLETHDATLIRGGGTFEQYYEFPNDLPFENLTQYPWD
IRRQDNPLYQQRITVMSGSDRDTVGILDGDFYSPFRFKGHDRPAMWLPGQRLIQGKFIDTHPIP
NTGRSGVHPNDFHTRGDGHGDTHRTHEERIYSLDTGLAAMPRAAHRPTLQPGPRTLSHAVRRPD
GSTVVTANACAYAYTQENPHQEPWSDLNVRHTMYRLAYQRQKGFQQPGDPLHIRTHACYGDGDV
TIPKEESLWPTVLGSCTEKSPACLESQIWCKTPNVDMVYGEHTPPLALWGMHAPPHVFLRMLA
QEGPPNVSTCRPAQSGQTFINQYGQFLLCFTMVWEVKPRPKSIKQWNPRPPISIPVGQSGPAFI
LDQDGYYRLPEHVWSARERIRSKR

FIG. 5

Pair-wise amino acid Identity comparisons

| | [ 1] | [ 2] | [ 3] | [ 4] | [ 5] | [ 6] | [ 7] | [ 8] | [ 9] | [10] | [11] | [12] | [13] | [14] | [15] | [16] |
|---|---|---|---|---|---|---|---|---|---|---|---|---|---|---|---|---|
| [ 1] Bovine | | 47.2% | 52.3% | 50.3% | 50.5% | 52.8% | 52.8% | 52.8% | 52.6% | 6.6% | 22.7% | 22.5% | 20.7% | 20.7% | 21.4% | 18.4% |
| [ 2] CanineMinute | 43.3% | | 51.0% | 60.2% | 61.0% | 50.5% | 51.3% | 50.5% | 51.8% | 7.4% | 25.0% | 24.7% | 21.7% | 21.7% | 20.9% | 18.1% |
| [ 3] GboV | 43.7% | 49.8% | | 50.0% | 50.3% | 91.3% | 83.7% | 83.7% | 84.2% | 6.6% | 23.7% | 23.7% | 21.7% | 21.7% | 23.0% | 17.6% |
| [ 4] PBoV1a | 42.8% | 53.5% | 49.1% | | 93.9% | 51.8% | 50.5% | 49.7% | 51.5% | 7.1% | 24.0% | 24.0% | 20.9% | 20.9% | 23.2% | 19.9% |
| [ 5] PBoV1b | 43.3% | 53.7% | 49.5% | 94.7% | | 51.8% | 51.3% | 49.7% | 51.8% | 7.9% | 24.5% | 24.5% | 20.4% | 20.4% | 23.0% | 20.2% |
| [ 6] HuBoca | 44.2% | 50.9% | 93.3% | 50.0% | 50.7% | | 82.7% | 82.7% | 83.2% | 6.9% | 24.2% | 24.2% | 21.2% | 21.2% | 22.5% | 17.9% |
| [ 7] HuBoca2 | 47.0% | 50.5% | 78.4% | 50.0% | 50.2% | 80.5% | | 91.8% | 91.1% | 7.9% | 23.5% | 23.2% | 20.9% | 20.9% | 22.5% | 18.4% |
| [ 8] HuBoca3 | 44.7% | 51.2% | 92.6% | 50.2% | 50.5% | 93.3% | 80.0% | | 92.1% | 8.7% | 24.0% | 23.7% | 21.7% | 21.7% | 23.2% | 18.6% |
| [ 9] HuBoca4 | 46.5% | 50.2% | 77.7% | 50.0% | 50.5% | 80.2% | 96.5% | 79.3% | | 8.2% | 23.5% | 23.7% | 21.4% | 21.4% | 23.2% | 19.1% |
| [10] Densovirus | 7.9% | 7.0% | 6.5% | 7.7% | 8.1% | 6.5% | 6.1% | 6.7% | 5.8% | | 7.7% | 7.4% | 8.4% | 8.2% | 6.9% | 6.6% |
| [11] Hokovirus_a | 20.5% | 20.7% | 20.5% | 22.6% | 22.3% | 20.9% | 20.2% | 20.7% | 20.5% | 7.9% | | 99.5% | 33.9% | 34.2% | 33.4% | 17.6% |
| [12] Hokovirus_b | 20.0% | 20.9% | 20.5% | 22.6% | 22.3% | 20.9% | 20.2% | 20.7% | 20.5% | 8.1% | 98.6% | | 33.9% | 34.2% | 33.4% | 17.9% |
| [13] PPV4a | 21.4% | 21.2% | 22.1% | 22.1% | 21.6% | 22.8% | 21.2% | 22.8% | 21.4% | 6.3% | 29.1% | 29.1% | | 99.5% | 51.3% | 17.1% |
| [14] PPV4b | 21.4% | 21.2% | 22.1% | 22.1% | 21.6% | 22.8% | 21.4% | 22.8% | 21.6% | 6.3% | 29.3% | 29.3% | 99.3% | | 51.3% | 17.1% |
| [15] BIVI_PPVSA | 22.1% | 22.3% | 23.3% | 23.3% | 23.0% | 22.8% | 23.0% | 22.3% | 23.3% | 5.1% | 32.6% | 32.3% | 60.5% | 60.2% | | 15.8% |
| [16] PPV1 | 18.6% | 25.4% | 23.3% | 20.5% | 21.2% | 22.8% | 26.1% | 23.5% | 25.1% | 5.8% | 16.5% | 16.5% | 18.4% | 18.4% | 19.3% | |

Top = VP1/CAP amino acid identity

Bottom = REP amino acid identity

Phylogenetic analysis of VP1/CAP region of PPV5A

FIG. 7

BLASTp results of PPV5A_Capsid vs. Total GenBank sequences.

```
Closest Match: Porcine Parvovirus 4 PPV4 -- GenBank Accession ID: AFM73871
Sequence Identities: 40% (310/774)
Sequence Homologies: 52% (403/774)

PPV5A  163  KHGDWPYLWGKDLDNAQRDEIIKALHSHVKVGTQLAGNIVRSIWKAKELLTEPVYELLKS  222
            KHG WP+LW   +D     EI + L    K+  +L  N + ++W+AKE +  P+YE++K
PPV4_  3    KHGHWPHLWAPFVDRQMSQEIQQVLKGSTKLSQKLLANFIIALWRAKEKIGAPIYEIVKG  62

PPV5A  223  ILPPSDLSKVPLPHSQQTDRTEDPETPGETRGTGSDSPRSPRPSGSTEDGGGPSSESRLP  282
            + P  D   V             P +P   RG+   SP    P+   ED
PPV4_  63   VFPSVDKKTVESLLPHPDPIPAPPSSP--QRGSKRASPPQ-SPNAHDED-----------  108

PPV5A  283  GSKVPVDPSATISEAKRQRTEEGMDISSCGPGGISASGAASNNSGLACGGGGGTNLGTES  342
                      T S  KRQ+T E    S C    +  +  A  +  L CG GGG      +
PPV4_  109  ----------TMSGHKRQKTMEVE--SECDKSLLCPTQNAGADFEL-CGTGGGATNEKGT  155

PPV5A  343  LVSGCQFGKNSVITSSFRRCLISPWPDKYCCSSAHDLIPGVVYETPWCYYDLNVISSYIF  402
             V G QF   S+ T   RRC++S +PD YC   + D IP +++ TPW YYDLN++S + F
PPV4_  156  WVGGTQFTDTSIRTFGIRRCVLSAFPDTYCSMMSGDAIPSIIFNTPWYYYDLNIMSCH-F  214

PPV5A  403  SPSAWQRLLEDYDAFRPKSLKVTIQSLVLKMSVKVQKKQT-TVQDSQSATIAIFEDKDYD  461
            SPSA+Q L+EDYDAFRP+SL V ++ LV+K   + Q  Q   V D+ SAT+  FED +Y+
PPV4_  215  SPSAFQTLIEDYDAFRPRSLTVHLKELVIKDVCQQQGLQAEQVSDNNSATLLAFEDVNYE  274

PPV5A  462  YPYVMGGGQKTVPGHLPGQPYNLPKYSYRTLGS-------VKESNRASMGGSGY------  508
             PYV+GGGQ +VPGHLPGQPY LPKYSYRT+G        V   N     G G+
PPV4_  275  LPYVLGGGQVSVPGHLPGQPYQLPKYSYRTVGKPDPNSGFVPGRNTHPDQGPGHPKASKT  334

PPV5A  509  ----TFKSNQDTELFLLETHDATLIRGGGTFEQYYEFPNDLPFENLTQYPWDIRRQDNPL  564
                 +   QDTE ++LE H AT++  G TF Q+Y FP DLPFE LTQY WD RRQDNPL
PPV4_  335  IWYSQYLETQDTEFYILENHKATILHSGNTFSQHYNFP-DLPFEQLTQYMWDARRQDNPL  393

PPV5A  565  YQQRITVMSGSDRD----TVGILDGDFYSPFRFKGHDRPAMWLPGQRLIQGKFIDTHPIP  620
              QRI VMS    D    T  I    +  PF  K   RPAM+L G R   G +  T P
PPV4_  394  IDQRIQVMSRMYDDGPQKIFAIKVNPYIVPFTVKSTSRPAMFLAGGRFKDGDYSITGPGD  453

PPV5A  621  NTGRSGVHPND---FHTRGDGHGDTHRTHEERIYSLDTGLAAMPRAAHRPTLQPGPRTLS  677
                S  + ND     TR     DT        Y +   LA   R       QPGPR
PPV4_  454  RDKTSFKYYNDPPWIITR-----DT--------YLFSSDLAKTERE------QPGPRQGD  494

PPV5A  678  HAVRRPDGSTVVTANACAYAYTQENPHQEPWSDLNVRHT-MYRLAYQRQKGFQQPGDPLH  736
              VR PDG+ +VT NA AY YT E     P           +RLA + ++G+  PG P H
PPV4_  495  TVVRTPDGTLIVTTNALAYGYTTEYLKNIPLLSSKYHGVENFRLAVENERGYSMPGHPSH  554

PPV5A  737  IRTHACYGD-----GDVTIPKE----ESLWPTVLGSCTEKSPACLESQIWCKTPNVDMVY  787
            IR     G       + TI   E    E  +P  +GS  EK+ A LESQIW + PN D+
PPV4_  555  IRETLFRGKLPSEIRESTIKSEDQRKEITFPDYMGSVNEKTTANLESQIWSQIPNTDITE  614

PPV5A  788  GEHTPPLALWGMHAPPPHVFLRMLAQEGPPNVSTCRPAQSGQTFINQYGQFLLCFTMVWE  847
```

FIG. 7 (Cont.)

```
               TPPL++WGM  PPP VFLR+LAQ GPP  S C  +    T++NQY QFLL + M W+
PPV4_  615  KCTTPPLSIWGMKNPPPMVFLRLLAQMGPPRRSACSGSIPSNTYLNQYCQFLLTYEMEWD  674

PPV5A  848  VKPRPKSIKQWNPRPPISIPVG-QSGPAFILDQDGYYRLPEHVWSARERIRSKR  900
            V  R +   +WNP PP  IP+G  + P +IL+++G YR+P  VW+A++R R +R
PPV4_  675  VIKRTRKTVRWNPIPPPQIPMGPNNLPVYILNKEGQYRMPTEVWTAKQRPRHRR  728
```

FIG. 8

BLASTp results of PPV5A_REP gene vs. Total GenBank sequences.

```
Closest Match: Porcine Parvovirus 4 PPV4 -- GenBank Accession ID: ADB20210
Sequence Identities: 58% (292/504)
Sequence Homologies: 73% (369/504)

PPV5A  15   LQVSYRGRPFSVRPLKRSGRCAGCR--KTPHLFFQLEKVDSKGGLHLHFCISVAAGTPRD  72
            L ++ R      R L++  R   CR    P +F QLE+VDSKGGLHLH+C+SV+AGTPRD
PPV4_  33   LVIAVRQAEALFRELQKELR-KSCRLGVDPGIFMQLEEVDSKGGLHLHWCVSVSAGTPRD  91

PPV5A  73   VSSMFKAIERRVSFYYFGVEGLTFFTPHKNKHGAWKSNDEGFIVNYLLKKLPLSECVYAW  132
            V ++FK  E++VS YYFGVEGL+FF PHKNKHGAWKS DEGFI NYLLKKLPL EC+YAW
PPV4_  92   VLTIFKNTEKKVSQYYFGVEGLSFFVPHKNKHGAWKSTDEGFIYNYLLKKLPLKECLYAW  151

PPV5A  133  TNMDGVIGDACLNEDKRRELLSERQDQGVIKELTAPTFKAATGDKMLSVVDWMCDNDVTT  192
            T + G IGDACLN DKR+ELL  RQD  VI+EL+AP +K ATG+KML +V W+ DN++ +
PPV4_  152  TTIGGAIGDACLNTDKRKELLDNRQDPAVIEELSAPMYKCATGEKMLDIVQWLVDNNICS  211

PPV5A  193  ERRWEEISAASLYSFLATPAGTHLAKQCLRAANQRIVSTKTSWLSLCKFASEKELRAFQN  252
            E RWE  +A SLYSFLAT AG ++AKQCLR A Q+++  K   L+L  F     LR FQ
PPV4_  212  ESRWENKNALSLYSFLATQAGGYMAKQCLRIAQQKLLKEKPLGLTLMDFKGMNALRRFQQ  271

PPV5A  253  GDPELSSDNNRIYYLFAMNNYCPDMASMIFFWWSMRQTGKRNSIWLFGPATTGKTNLASA  312
             + E++ DNNR++Y+FA+NNY P +AS+I ++WSM+QTGKRN +W +GPATTGKTN+A A
PPV4_  272  DEGEMTFDNNRMHYIFAINNYDPKIASVIMYFWSMKQTGKRNCVWFYGPATTGKTNMAQA  331

PPV5A  313  IAHTAASYGCVNWNNANFPFQDIVNVQLGWWEEGKMTEDVVECAKALLGGSNVRVDRKCM  372
            I H++A+YG VNWNNANFPFQDIV  Q+GWWEEGKMT D+VE AKALLGG+ +R+DRKCM
PPV4_  332  ICHSSANYGNVNWNNANFPFQDIVGAQVGWWEEGKMTGDMVEAAKALLGGTALRIDRKCM  391

PPV5A  373  QSAEVQSPPFIITSNTDMCLVSQGSYISFEHQQPLQDRMIKFEFNHVLPGNFGLISEDEV  432
            QS EV SPPF+ITSN DM +V +GS++SFEHQQPL+DRMIKF FN  LPGNFGLI+ +EV
PPV4_  392  QSIEVNSPPFLITSNVDMTIVQEGSFVSFEHQQPLEDRMIKFSFNMTLPGNFGLITSEEV  451

PPV5A  433  VAFFRNGAYNVLKHAYMRKAQLFALGPASLPYKPPTGELVCIDQAKSPSPSASRRSVRNW  492
             +FFR GA  +     +    +F  GPAS+ +  P GE+        P      +    +
PPV4_  452  KSFFRMGA-KLAAQPDIMNCPIFKKGPASIRHLVPVGEI-------PPPKEMKHKRQPLY  503

PPV5A  493  MTCPPDPVQDDPAELDEYFPPDTP  516
            M   PD +QD+P ELD +F  + P
PPV4_  504  MRAEPDEIQDNPEELDHWFEEEAP  527
```

PORCINE PARVOVIRUS 5A, METHODS OF USE AND VACCINE

SEQUENCE LISTING

This application contains a sequence listing in accordance with 37 C.F.R. 1.821-1.825. The sequence listing accompanying this application is hereby incorporated by reference in its entirety. Said ASCII copy, created on Mar. 11, 2013, is named 10-0150-SEQ.txt and is 34,532 bytes in size.

BACKGROUND OF THE INVENTION

A. Field of the Invention

The present invention is in the field of animal health and relates to novel porcine parvovirus strains, including attenuated strains for vaccination, methods of manufacture and methods of treatment using vaccines obtained from said novel parvovirus strains.

B. Description of the Related Art

Parvoviruses infect a wide variety of animal species, and some of them are responsible for severe clinical diseases, but the majority of these viruses cause only mild or subclinical infections. They belong to the family Parvoviridae and form two subfamilies: Densovirinae, whose members infect insects, and Parvovirinae, whose members infect vertebrates. The latter subfamily currently includes five genera: Dependovirus, Erythrovirus, Amdovirus, Bocavirus and Parvovirus (1).

Parvovirus virions are non-enveloped and contain single-stranded, linear DNA genomes of approximately 5-6 kilobases (kb). The genome consists of two main open reading frames (ORF) that encode the non-structural and capsid proteins. The newly described bocaviruses carry a third ORF, between the two major ORFs (1).

The classical porcine parvovirus (PPV1) strains of the genus Parvovirus are widely distributed around the world and are responsible for reproductive disorders of pigs, especially in herds where vaccination protocols are not followed correctly or vaccine efficacy is decreased due to immunosuppressive factors. During the last decade, a number of new parvoviruses have been detected in pigs. These include porcine parvovirus 2 (PPV2) (2) and related viruses (3). A new group of porcine and bovine parvoviruses, namely the hokoviruses (PHoV, BHoV), were identified in Hong Kong (4), and these viruses were found to be genetically similar to human PARV4 and 5. Although they were originally named hokoviruses after Hong Kong, a new classification of PHoV as PPV3 was proposed (5). PPV4 shows the highest similarity to bovine parvovirus 2, but the coding capacity and genome organization are similar to those of bocaviruses, as PPV4 encodes an additional ORF3 like bocaviruses, located between ORF1 and ORF2. The PPV4-encoded putative ORF3 protein, however, is quite different from that of bocaviruses (5).

There is an ongoing need to monitor swine for the emergence of new viruses, and to develop vaccines, treatments and methods of detection for new viruses.

SUMMARY OF THE INVENTION

The present invention provides novel nucleotides sequences, protein sequences, immunogenic compositions, vaccines, and methods that relate to making and using new parvovirus strains that infect, inter alia, domestic swine. These strains are related to the novel porcine parvovirus identified in tissue samples from clinically diseased domestic swine; based on sequence homology with known porcine parvovirus species and strains, the novel virus was denominated porcine parvovirus 5A or PPV5A.

The compositions and methods of the invention provide for the detection of infections by said new virus, monitoring genetic changes in the viral sequences in wild and domestic animals and herds, and making and using novel vaccines for protecting animals from infection by the virus.

Immunogenic compositions and vaccines of the invention comprise polypeptide sequences encoded by the nucleic acid sequence of SEQ ID NO:1, or immunogenic fragments thereof, optionally including adjuvants for inducing a more robust immunogenic response.

Exemplary compositions of the invention comprise any one of the polypeptide sequences of SEQ ID NO:2, SEQ ID NO:3, SEQ NO:4, or fragments thereof that are immunoreactive to antibodies specific for PPV5A. Preferred polypeptides of the invention include the sequences of SEQ ID NO:2 or SEQ ID NO:4, in particular SEQ ID NO:4. Preferably those polypeptides, or fragments thereof, are immunoreactive to antibodies specific for PPV5A.

In another aspect the invention provides nucleic acid sequences that encode one or more polypeptides, antibody constructs, or antibody conjugates. The gene sequences coding for the polypeptides comprise a nucleic acid sequence that is at least 95%, 90%, 85%, or even 80% homologous to and/or identical with the sequence of SEQ ID NO: 1, in particular, nucleotide sequences 2845-5547 of SEQ ID NO:1 (the capsid protein), or fragments of SEQ ID NO:1 coding for a polypeptide that is immunoreactive to antibodies specific for PPV5A. Exemplary nucleic acid sequences of the invention include any one of the sequences of nucleotides 1975-2844 of SEQ ID NO:1, and nucleotides 2845-5547 of SEQ ID NO:1, and fragments thereof, that encode a polypeptide that is immunoreactive to an antibody specific for PPV5A. Preferably, the nucleic acid sequences, or genes, are those coding for a polypeptide or peptide that is immunoreactive to an antibody specific for PPV5A.

Moreover a polypeptide of the invention as used herein includes but is not limited to a polypeptide that comprises:

i) a polypeptide comprising the amino acid sequence of SEQ ID NO: 2 or SEQ ID NO:4;

ii) a polypeptide that is at least 80% homologous to and/or identical with a polypeptide of i);

iii) a fragment of the polypeptides of i) and/or ii);

iv) a fragment of iii) or iv) comprising at least 5, preferably 8, more preferably 10, even more preferably 15 contiguous amino acids included in the sequences of SEQ ID NO: 2 or SEQ ID NO:4;

v) a polypeptide that is encoded by a polynucleotide comprising the sequence of nucleotides 1975-2844 of SEQ ID NO:1, or nucleotides 2845-5547 of SEQ ID NO:1;

vi) a polypeptide that is encoded by a polynucleotide that is at least 80% homologous to or identical with polynucleotide of vi);

vii) a protein fragment that is encoded by a polynucleotide that comprises at least 15, preferably 24, more preferably 30, even more preferably 45 contiguous nucleotides included in the sequences of nucleotides 1975-2844 of SEQ ID NO:1, or nucleotides 2845-5547 of SEQ ID NO:1.

Immunogenic compositions of the invention which comprise at least one or more PPV5A polypeptides as defined herein may further comprise a physiologically-acceptable vehicle such as a pharmaceutically or veterinary-acceptable carrier, adjuvant, or combination thereof.

Any of the PPV5A polypeptides provided herewith or any immunogenic compositions comprising one or more of these PPV5A polypeptides provided herewith can be used as a medicament, preferably as a vaccine or immunogenic composition, most preferably for the prophylaxis or treatment of a subject against a PPV5A infection.

Particularly preferred PPV5A polypeptides include those with immunogenic epitopes that induce an immunological response that is specific for PPV5A. Preferred PPVA polypeptides include those having an amino acid sequences predicted in related PPV1 to be surface antigens (Simpson et al. JMB 315, 2002) and include, but is not limited to residues 141-156, 272-278, and 329-339 of SEQ ID NO:4.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a PPV5A infection in a subject comprising the step of administering to the subject an immunogenic composition comprising one or more PPV5A polypeptides as defined herein. Preferably, the immune response is provoked against more than one serotype or strain of PPV5A. Compositions of the invention may be used to treat or alternatively to prevent a PPV5A infection. Preferably, such immune response reduces the incidence of or severity of one or more clinical signs associated with or caused by the infection with one or more PPV5A serotypes.

Herein, suitable subjects and subjects in need to which compositions of the invention may be administered include animals in need of either prophylactic or treatment for a viral, microbial, parasitic, protozoan, bacterial, or fungal associated infection, disease, or condition. Animals in which the immune response is stimulated by use of compositions or methods of the invention include livestock, such as porcine, bovine, poultry (e.g. chickens, ducks, geese, or turkeys) caprine, and ovine, and domestic animals, such as mice, rabbits, dogs, cats, and horses. Preferred animals include swine, murids, equids, lagomorphs, and bovids. Most preferably, an immune response is stimulated in swine.

The invention also provides a method of reducing the incidence of or severity of one or more clinical signs associated with or caused by PPV5A infection, comprising the step of administering an immunogenic composition of the invention that comprises one or more PPV5A peptides as provided herewith and preferably a carrier molecule, such that the incidence of or the severity of a clinical sign of the PPV5A infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs include viremia and immunosuppression as a result from an infection with PPV5A alone. Such clinical signs may include neurological signs (depression, ataxia, lethargy), diarrhea, dyspnea, loss of body condition, swelling of joints (resulting in lameness and recumbency), decreased average daily weight gain, mortality, and polyserositis as a result of a co-infection with another organism, e.g., *Mycoplasma hyorhinis.*

According to a further aspect, the present invention also relates to a method for the prophylaxis of a PPV5A infection, wherein said PPV5A infection may be caused by PPV5A having 100% sequence identity with the nucleotide sequences of SEQ ID NOs 1, 2, 3 and/or 4, having at least 95% sequence identity with the nucleotides sequences of SEQ ID NOs 1, 2, 3 and/or 4, having at least 90% sequence identity with the nucleotides sequences of SEQ ID NOs 1, 2, 3 and/or 4, or having at least 85% sequence identity with the nucleotides sequences of SEQ ID NOs 1, 2, 3 and/or 4, comprising the step of administering an immunogenic composition of the invention that comprises one or more PPV5A peptides as provided herewith.

The invention also provides a method of preparing any of the immunogenic compositions provided herewith that method comprises mixing one or more PPV5A peptides as provided herewith with a carrier molecule, preferably such that the one or more PPV5A peptides and carrier molecule are covalently coupled or conjugated to one another. Such conjugates may be multivalent or univalent. Multivalent compositions or vaccines include an immuno-conjugation of multiple PPV5A peptides with a carrier molecule. In a further aspect, the invention provides a method of producing one or more PPV5A peptides that method comprises transforming a host cell, preferably a prokaryotic cell such as *E. coli* with a nucleic acid molecule that codes for any of the PPV5A peptides as provided herewith. Alternatively, the host cell may be a eukaryotic cell such as an animal cell, an insect cell, a protist cell, a plant cell, or a fungal cell. Preferably the eukaryotic cell is a mammalian cell such as CHO, BHK or COS, or a fungal cell such as *Saccharomyces cerevisiae*, or an insect cell such as Sf9. Baculovirus expression of the nucleic acids of the instant invention are also preferred.

Another aspect of the invention provides a method of producing one or more PPV5A peptides that induce an immune response against at least one genetic variants of PPV5A and more preferably two or more genetic variants of PPV5A. This comprises culturing a transformed expression vector coding for and expressing one or more PPV5A peptides disclosed herein. The expressed proteins are either retained by the expression organism or secreted into the culture medium. Expression is conducted under conditions sufficient to produce a PPV5A peptide capable of inducing an immune response to PPV5A. The PPV5A serotypes to which the PPV5A peptides induce an immune response include but are not limited to sequences having at least 99, 98, 97, 96, 95, 94, 93, 92, 91 or 90% identity.

Methods of making compositions of the invention may further comprise admixing the conjugate of one or more PPV5A peptides and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method of diagnosing a PPV5A infection in a subject. That method comprises providing one or more PPV5A peptides; contacting the one or more PPV5A peptides with a sample obtained from the subject; and identifying the subject as having a PPV5A infection if an antibody capable of binding the one or more PPV5A peptides is detected in the sample.

In another respect, the invention provides a method of ascertaining that a subject has been previously exposed to a PPV5A infection and is able to express an immune response to PPV5A. That method comprises providing one or more PPV5A peptides; contacting the one or more PPV5A peptides with a sample obtained from the subject; and identifying the subject as having a PPV5A infection if an antibody capable of binding the one or more PPV5A peptides is detected in the sample.

The invention also provides kits that comprise an immunogenic composition that comprises one or more PPV5A peptides, preferably together with a carrier molecule; a container for packaging the immunogenic composition; a set of printed instructions; and a dispenser capable of administering the immunogenic composition to an animal. Optionally, the one or more PPV5A peptides and the carrier molecule may be packaged as a conjugate or as separate compounds. When supplied separately, a means of conjugating the one or more PPV5A peptides and carrier molecule, as well as appropriate printed instructions, is also supplied.

The invention also provides kits for vaccinating an animal comprising a set of printed instructions; a dispenser capable of administering the immunogenic composition provided herewith comprising one or more PPV5A peptides to an animal; and wherein at least one of PPV5A peptides effectively immunizes the animal against at least one disease associated with PPV5A infection. Preferably, the one or more PPV5A peptides are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the PPV5A peptides as provided herewith included in the kit is capable of reducing the severity of at least one clinical sign of a PPV5A infection when administered intranasally, orally, intradermally, or intramuscularly to an animal. Preferably, the severity of a clinical sign is reduced by at least 10% preferably by at least 20%, even more preferred by at least 30%, even more preferred by at least 50%, even more preferred by at least 70%, most preferred by at least 100% as compared to an untreated, infected animal.

Methods for the treatment or prophylaxis of infections caused by PPV5A are also disclosed. The method comprises administering an effective amount of the immunogenic composition of the present invention to a subject, wherein said treatment or prophylaxis is selected from the group consisting of reducing signs of PPV5A infection, reducing the severity of or incidence of clinical signs of PPV5A infection, reducing the mortality of subjects from PPV5A infection, and combinations thereof.

Compositions of the invention further comprise a veterinary-acceptable carrier, adjuvant, or combination thereof. Such compositions may be used as a vaccine and comprise one or more additional attenuated vaccines, inactivated vaccines, or combinations thereof. Such vaccines elicit a protective immunological response against at least one disease associated with viruses selected from the group consisting of porcine parvoviruses 1, 2, 3, 4, 5A, 5B, other porcine parvovirus species, other porcine pathogenic viruses and bacteria, and combinations thereof. Other types of vaccines that could be co-administered in combination with a vaccine to PPV5A include, but are not limited to, porcine circovirus type 2 (e.g., INGELVAC® CircoFLEX, INGELVAC® CircoFLEX-MycoFLEX), porcine reproductive and respiratory syndrome virus (e.g., INGELVAC® PRRS ATP, INGELVAC® PRRSV MLV,), porcine parvovirus (e.g., REPROCYC® PRRSV-PLE), *Mycoplasma* (e.g., INGELVAC® MycoFLEX), etc.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

The invention also provides a method of reducing the severity of an ongoing PPV5A infection in an animal by administration of a composition to the animal. The composition may include an attenuated viral culture or one or more PPV5A peptides in combination with an acceptable veterinary carrier.

Preferred routes of administration include intranasal, oral (e.g., in drinking water), intradermal, and intramuscular. Intramuscular administration, most preferably in a single dose, is preferred. The skilled artisan will recognize that compositions of the invention may also be administered in two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one isolate from a cell culture, including but not limited to a bacterial, fungal, insect or mammalian cell culture that effectively immunizes the animal against at least one disease associated with PPV5A, other parvovirus strains, other pathogens, and/or a combination thereof. Kits of the invention may further comprise a veterinary-acceptable carrier, adjuvant, or combination thereof.

The dispenser in a kit of the invention is capable of dispensing its contents as droplets; and the isolate included in the kit is capable of reducing the severity of at least one clinical sign of a PPV5A infection when administered intranasally, orally, intradermally, or intramuscularly to an animal. In some kits, the isolate is also capable of reducing the severity of at least one clinical sign of a PPV5A infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. shows the nucleic acid sequence of PPV5A (SEQ ID NO:1).

FIG. 2. shows the protein sequence of the PPV5A replicase (SEQ ID NO:2).

FIG. 3. shows the protein sequence of the PPV5A open reading frame (ORF) protein (SEQ ID NO:3).

FIG. 4. shows the protein sequence of the PPV5A capsid protein (SEQ ID NO:4).

FIG. 5. shows pair-wise amino acid identity comparisons of the protein sequences of the PPV5A capsid protein and numerous other viral sequences. References for the viral sequences are listed in Table 1:

TABLE 1

Figure 6:
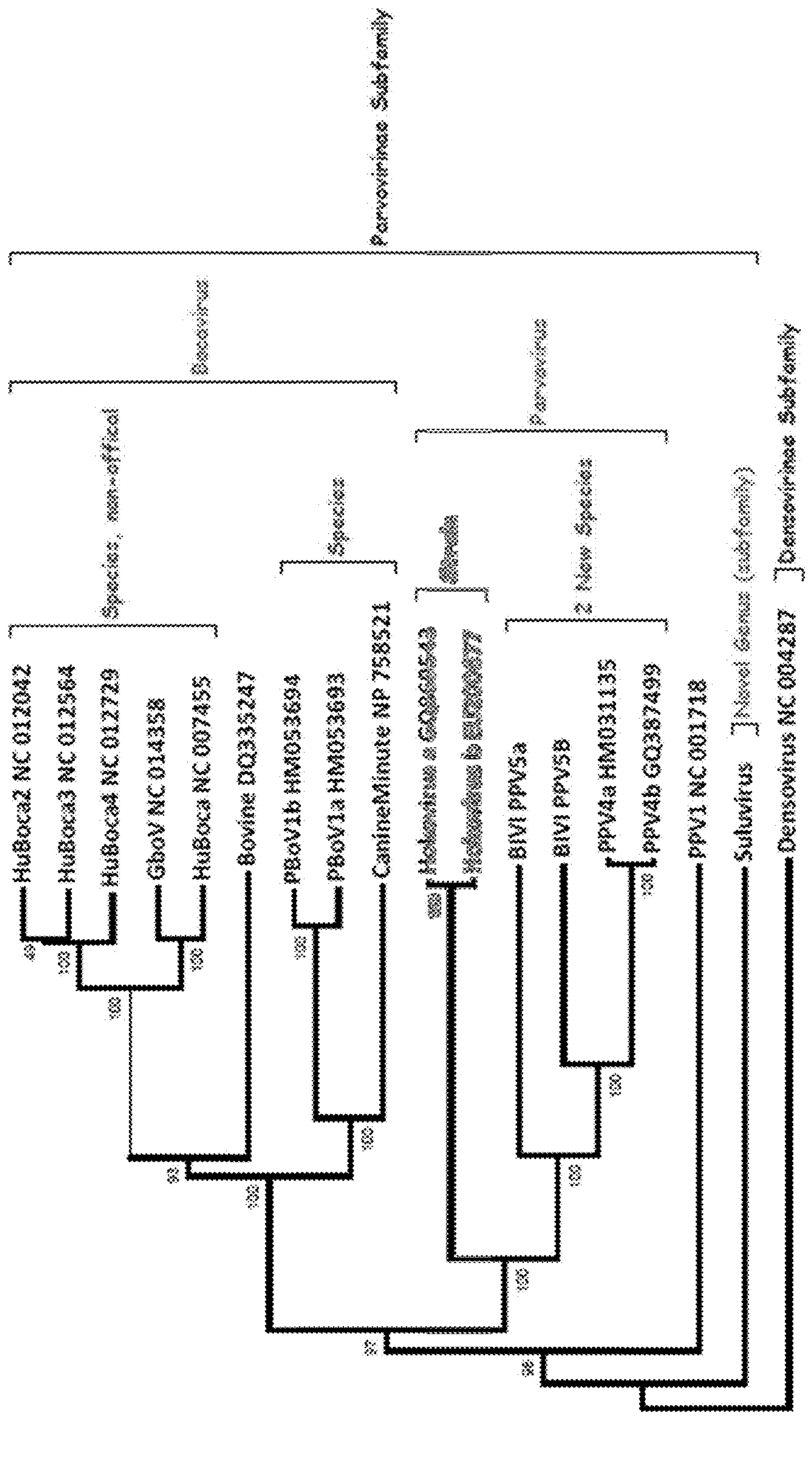

| Sequence | GenBank ID | Journal Info | Authors |
|---|---|---|---|
| [1] Bovine | DQ_335247 | J. Virol. 81 (21), 12080-12085 (2007) | Qiu, J., Cheng, F., Johnson, F. B. and Pintel, D |
| [2] Canine-Minute | NP_758521 | Virology 302 (2), 219-223 (2002 | Schwartz, D., Green, B., Carmichael, L. E. and Parrish, C. R. |
| [3] GboV | NC_014358 | PLoS ONE 5 (7), E11948 (2010) | Kapoor, A., Mehta, N., Esper, F., Poljsak-Prijatelj, M., Quan, P. L., Qaisar, N., Delwart, E. and Lipkin, W. I |
| [4] PBoV1a | HM_053693 | PLoS ONE 5 (10), E13583 (2010) | Cheng, W. X., Li, J. S., Huang, C. P., Yao, D. P., Liu, N., Cui, S. X., Jin, Y. and Duan, Z. J. |
| [5] PBoV1b | HM_053694 | PLoS ONE 5 (10), E13583 (2010) | Cheng, W. X., Li, J. S., Huang, C. P., Yao, D. P., Liu, N., Cui, S. X., Jin, Y. and Duan, Z. J. |
| [6] HuBoca | NC_007455 | Proc. Natl. Acad. Sci. U.S.A. 102 (36), 12891-12896 (2005) | Allander, T., Tammi, M. T., Eriksson, M., Bjerkner, A., Tiveljung-Lindell, A. and Andersson, B. |
| [7] HuBoca2 | NC_012042 | J. Infect. Dis. 199 (2), 196-200 (2009 | Kapoor, A., Slikas, E., Simmonds, P., Chieochansin, T., Naeem, A., Shaukat, S., Alam, M. M., Sharif, S., Angez, M., Zaidi, S. and Delwart, E. |
| [8] HuBoca3 | NC_012564 | PLoS Pathog. 5 (4), E1000391 (2009) | Arthur, J. L., Higgins, G. D., Davidson, G. P., Givney, R. C. and Ratcliff, R. M. |
| [9] HuBoca4 | NC_012729 | J. Infect. Dis. 201 (11), 1633-1643 (2010) | Kapoor, A., Simmonds, P., Slikas, E., Li, L., Bodhidatta, L., Sethabutr, O., Triki, H., Bahri, O., Oderinde, B. S., Baba, M. M., Bukbuk, D. N., Besser, J., Bartkus, J. and Delwart, E. |
| [10] Denso-virus | NC_004287 | DIRECT SUBMISSION TO GENBANK | Nonaka, K., Chiba, T., Nakahara, S., Kajiura, Z. and Nakagaki, M. |
| [11] Hoko-virus_a | GQ_869543 | Virol. J. 7, 171 (2010) | Adlhoch, C., Kaiser, M., Ellerbrok, H. and Pauli, G. |
| [12] Hoko-virus_b | EU_200677 | J. Gen. Virol. 89 (PT 8), 1840-1848 (2008) | Lau, S. K., Woo, P. C., Tse, H., Fu, C. T., Au, W. K., Chen, X. C., Tsoi, H. W., Tsang, T. H., Chan, J. S., Tsang, D. N., Li, K. S., Tse, C. W., Ng, T. K., Tsang, O. T., Zheng, B. J., Tam, S., Chan, K. H., Zhou, B. and Yuen, K. Y. |
| [13] PPV4a | HM_031135 | Virol. J. 7 (1), 333 (2010) | Huang, L., Zhai, S. L., Cheung, A. K., Zhang, H. B., Long, J. X. and Yuan, S. S |
| [14] PPV4b | GQ_387499 | Arch. Virol. 155 (5), 801-806 (2010) | Cheung, A. K., Wu, G., Wang, D., Bayles, D. O., Lager, K. M. and Vincent, A. L. |
| [15] PPV5A | | | |
| [16] PPV1 | NC_001718 | Virology 197 (1), 86-98 (1993) | Bergeron, J., Menezes, J. and Tijssen, P. |

FIG. 6 shows a phylogenetic analysis of VP1/CAP region of PPV5A as compared with other viral VP1 and capsid proteins listed in Table 1.

FIG. 7 shows identities of the PPV5A capsid protein (residues 55-792 of SEQ ID NO:4) to the closest related protein of PPV4 (GenBank accession # AFM73871 (SEQ ID NO: 5)), showing a sequence identity of 40% (310/774).

FIG. 8 shows identities of the PPV5A replicase protein (residues 15-516 of SEQ ID NO:2) to the closest related protein of PPV4 (GenBank accession # ADB20210 (SEQ ID NO: 11)), showing a sequence identity of 58% (292/504).

DETAILED DESCRIPTION

The invention provides nucleic acids and fragments thereof, polypeptides and immunologically-effective fragments thereof, vaccines, immunologically-effective preparations, antibodies, diagnostic assays and kits, and methods of making and using said compositions and preparations, related to the herein-disclosed novel porcine parvovirus 5A and variants thereof.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984);

Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms “a”, “an” and “the” include plural referents unless the content clearly dictates otherwise. Thus, for example, reference to “an antigen” includes a mixture of two or more antigens, reference to “an excipient” includes mixtures of two or more excipients, and the like.

A. Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of “or” means “and/or” unless stated otherwise. Furthermore, the use of the term “including”, as well as other forms such as “includes” and “included” is not limiting. All patents and publications referred to herein are incorporated by reference herein.

“Protection against disease,” “protective immunity,” “functional immunity” and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, “reduction of the incidence and/or severity of clinical signs” or “reduction of clinical symptoms” means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of infection with PPV5A. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term “increased protection” herein means, but is not limited to, a significant reduction of one or more clinical symptoms which are associated with infection by an infectious agent, preferably PPV5A, in a vaccinated group of subjects vs. a non-vaccinated control group of subjects. The term “significant reduction of clinical symptoms” means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

“Long-lasting protection” shall refer to “improved efficacy” that persists for at least 3 weeks, but more preferably at least 3 months, still more preferably at least 6 months. In the case of livestock, it is most preferred that the long lasting protection shall persist until the average age at which animals are marketed for meat.

An “immunogenic or immunological composition” refers to a composition of matter that comprises at least one PPV5A protein or polypeptide, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a PPV5A infection.

An “immunogenic” PPV5A polypeptide, or “antigen” as used herein refer to a polypeptide or protein that elicits an immunological response as described herein. An “immunogenic” PPV5A protein or polypeptide includes the full-length sequence of any of the coding sequences identified herein or analogs or immunogenic fragments thereof. The term “immunogenic fragment” or “immunogenic portion” refers to a fragment or truncated and/or substituted form of an amino acid sequence of a PPV5A protein that includes one or more epitopes and thus elicits the immunological response described herein. In general, such truncated and/or substituted forms, or fragments will comprise or encode at least six contiguous amino acids from the full-length protein, e.g., the capsid protein. More preferably, the truncated or substituted forms, or fragments will have at least 10, more preferably at least 15, and still more preferably at least 19, and even more preferably 30 contiguous amino acids from the full-length protein, e.g., the capsid protein.

The term “epitope” means a segment or fragment of a composition of matter, e.g., a protein or polypeptide, which is recognized by the immune system, specifically by antibodies, B cells, or T cells. In the present invention, the epitope is generally a fragment or fragments of a polypeptide sequence of a viral protein.

Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc.

Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of PPV5A infection but does not react with an antigen characteristic of a strict challenge control. To determine the specificity of a potential PPV5A immunoreactive protein or other polypeptide, various immunoassays (ELISA, IFA, WesternBlot) would be used to test the protein against animal sera containing genetically similar viruses. The protein would also be tested in various immunoassays against material containing proteins related to the expression method (Baculovirus, Sf9 cells, etc.).

As used herein, "a pharmaceutical- or veterinary-acceptable carrier" or "excipient" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 500 μg to about 5 mg per dose, more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a live viral-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—an immune response in the animal against PPV5A.

"Mortality", in the context of the present invention, refers to death caused by PPV5A infection, and/or co-infections with other organisms which are potentiated by PPV5A infections, and includes the situation where the infection is so severe that an animal is euthanized to prevent suffering and provide a humane ending to its life.

"Attenuation" means reducing the virulence of a pathogen. In the present invention "attenuation" is synonymous with "avirulent." In the present invention, an attenuated virus is one in which the virulence has been reduced so that it does not cause clinical signs of a PPV5A infection but is capable of inducing an immune response in the target mammal, but may also mean that the clinical signs are reduced in incidence or severity in animals infected with the attenuated PPV5A in comparison with a "control group" of animals infected with non-attenuated PPV5A and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent PPV5A strain is one that suitable for incorporation into an immunogenic composition comprising a modified live PPV5A virus.

"Killed" or "inactivated" means treated with a physical or chemical agent which renders the PPV5A virus dead and/or otherwise incapable of reproduction. PPV5A may be killed by conventional means, such as, for example, heat, radiation or psoralen in the presence of ultraviolet light. PPV5A can be inactivated by conventional means such as, for example, through chemical inactivation using one or more chemical inactivating agents including, but not limited to, one or more of binary ethyleneimine (BEI), beta-propiolactone, formalin, gluteraldehyde, and/or sodium dodecyl sulfate. Methods of attenuating virulent strains of these viruses and methods of making an inactivated viral preparation are known in the art and are described in, e.g., U.S. Pat. Nos. 4,567,042 and 4,567,043. Antigens from PPV5A for use in the vaccine compositions of the present invention can thus be in the form of a whole virus which is a modified and/or attenuated live viral preparation or a killed or inactivated viral preparation, inter alia.

"Antibodies" as used herein includes anti-PPV5A antibodies, e.g., monoclonal and polyclonal antibodies, single chain antibodies, chimeric antibodies, humanized, human, porcine, and CDR-grafted antibodies, including compounds which include CDR sequences which specifically recognize a PPV5A polypeptide of the invention. The term "specific for" indicates that the variable regions of the antibodies of the invention recognize and bind a PPV5A polypeptide exclusively (i.e., are able to distinguish a single PPV5A polypeptide from related polypeptides despite sequence identity, homology, or similarity found in the family of polypeptides), and which are permitted (optionally) to interact with other proteins (for example, *S. aureus* protein A or other antibodies in ELISA techniques) through interactions with sequences outside the variable region of the antibodies, and in particular, in the constant region of the antibody molecule. Screening assays to determine binding specificity of an antibody of the invention are well known and routinely practiced in the art. For a comprehensive discussion of such assays, see Harlow et al. (Eds), Antibodies A Laboratory Manual: Cold Spring Harbor Laboratory; Cold Spring Harbor, N.Y. (1988), Chapter 6. Antibodies that recognize and bind fragments of the PPV5A polypeptides of the invention are also contemplated, provided that the antibodies are first and foremost specific for, as defined above, a PPV5A polypeptide of the invention from which the fragment was derived. For the purposes of clarity, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. Antibodies can exist in a variety of forms including, for example, as, Fv, Fab', F(ab')2, as well as in single chains, and include synthetic polypeptides that contain all or part of one or more antibody single chain polypeptide sequences.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount an attenuated live virus preparation, as measured by the number of plaque forming units (PFU) per dose or equivalent measure, is monitored by the median tissue culture infective dose (TCID50), i.e. the amount of a pathogenic agent that will produce pathological change in 50% of inoculated and susceptible cell cultures. For a killed vaccine or antigenic subunit, the effective amount refers to the relative antigen content (RAC), i.e. the inclusion level of antigen per effective dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences, with gaps introduced if necessary. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988); the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and BLASTX (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology" as used herein refers to a method of determining the relatedness of two sequences. To determine sequence homology, two or more sequences are optimally aligned, and gaps are introduced if necessary. However, in contrast to "sequence identity," conservative amino acid substitutions are also counted as a match when determining sequence homology. In other words, to obtain a polypeptide having 95% sequence homology with a reference sequence, 85%, preferably 90%, even more preferably 95% of the amino acid residues in the reference sequence must match or comprise a conservative substitution with another amino acid, or a number of amino acids up to 15%, preferably up to 10%, even more preferably up to 5% of the total amino acid residues, not including conservative substitutions, in the reference sequence may be inserted into the reference sequence. Preferably the homologous sequence comprises at least a stretch of 50, even more preferred of 100, even more preferred of 250, even more preferred of 500 nucleotides encoding homologous amino acids.

A "conservative substitution" refers to the substitution of an amino acid residue with another amino acid residue having similar characteristics or properties including size, hydrophobicity, etc., such that the overall functionality does not change significantly. It can also mean a nucleotide substitution that results in a conservative amino acid substitution.

B. Carrier Molecules

The carrier molecules to which the PPV5A proteins or peptides of the invention can be conjugated or covalently linked are preferably those described above. Preferred carriers for animal use are bovine serum albumin and Keyhole Limpet Hemocyanin. Preferably, the carrier protein itself is an immunogen.

The PPV5A proteins or peptides of the invention may be covalently coupled to the carrier by any convenient method known to the art. While use of a symmetric linker such as adipic acid dihydrazide, as described by Schneerson et al, J. Experimental Medicine, 152, 361-376 (1980), or a heterobifunctional linker such as N-succinimidyl 3-(2-pyridyldithio) propionate as described by Fattom et al, Infection and Immunity, 56, 2292-2298 (1988) are within the scope of the invention, it is preferred to avoid the use of any linker but instead couple a PPV5A peptide of the invention directly to the carrier molecule. Such coupling may be achieved by means of reductive amination as described by Landi et al J. Immunology, 127, 1011-1019 (1981).

The size of the immunogenic composition, as defined by average molecular weight, is variable and dependent upon the chosen PPV5A protein(s) or peptide(s) and the method of coupling of the PPV5A protein(s) or peptide(s) to the carrier. Therefore, it can be as small as 1,000 daltons ($10^3$) or greater than $10^6$ daltons. With the reductive amination coupling method, the molecular weight of the PPV5A protein(s) or peptide(s) is usually within the range of 5,000 to 500,000 or more; e.g., for the capsid protein of SEQ ID NO:4, the molecular weight is predicted to be approximately 80,000 daltons, which is predicted to form virus like particles (VLP) comprised of 60 monomeric proteins.

Carrier molecules, i.e. peptides, derivatives and analogs thereof, and peptide mimetics that specifically bind a PPV5A protein or peptide of the invention can be produced by various methods known in the art, including, but not limited to solid-phase synthesis or by solution (Nakanishi et al., 1993, Gene 137:51-56; Merrifield, 1963, J. Am. Chem. Soc. 15:2149-2154; Neurath, H. et al., Eds., The Proteins, Vol II, 3d Ed., p. 105-237, Academic Press, New York, N.Y. (1976), incorporated herein in their entirety by reference).

The PPV5A proteins or peptides of the invention or the antibodies or binding portions thereof of the present invention may be administered in injectable dosages by solution or suspension of in a diluent with a pharmaceutical or veterinary carrier.

Safety and efficacy of such molecules are determined by standard procedures in cell cultures or experimental animals as described and regulated by the Center for Veterinary Biologics (CVB). Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immunoconjugation of multiple PPV5A proteins or peptides with a carrier molecule.

In one aspect, the PPV5A protein or peptide compositions comprise an effective immunizing amount of the immunogenic conjugate, preferably in combination with an immunostimulant; and a physiologically acceptable vehicle. As used in the present context, "immunostimulant" is intended to encompass any compound or composition which has the ability to enhance the activity of the immune system, whether it is a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of stimulant for a given vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig.

C. Adjuvants

In order to further increase the immunogenicity of the immunogenic compositions provided herewith, and which contain one or more PPV5A proteins or peptides may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the PPV5A protein(s) or peptide(s) under appropriate sterile conditions in accordance with known techniques to produce the adjuvanted composition. Complexation of the PPV5A proteins(s) or peptide(s) and the adjuvant is facilitated by the existence of a net negative charge on the conjugate which is electrostatically attracted to the positive charge present on the long chain alkyl compound adjuvant.

D. Physiologically-Acceptable Vehicles

The vaccine compositions of this invention may be formulated using techniques similar to those used for other pharmaceutical polypeptide compositions. Thus, the adjuvant and PPV5A protein(s) or peptide(s), preferably conjugated to carrier molecule and/or admixed with an adjuvant may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably about 1.0 ml at the concentrations of conjugate and adjuvant noted above.

The vaccine compositions of the invention may be administered by any convenient means.

E. Formulation

Immunogenic conjugates comprising a PPV5A protein(s) or peptide(s) coupled to a carrier molecule can be used as vaccines for immunization against one or more serotypes of PPV5A. The vaccines, comprising the immunogenic conjugate in a physiologically acceptable vehicle, are useful in a method of immunizing animals, preferably swine, for treatment or prevention of infections by PPV5A.

Antibodies generated against immunogenic conjugates of the present invention by immunization with an immunogenic conjugate can be used in passive immunotherapy and generation of antiidiotypic antibodies for treating or preventing infections of PPV5A.

The subject to which the composition is administered is preferably an animal, including but not limited to cows, horses, sheep, pigs, poultry (e.g., chickens), goats, cats, dogs, hamsters, mice and rats; most preferably pigs.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

F. Effective Dose

The compounds described herein can be administered to a subject at therapeutically effective doses to treat PPV5A-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subject's circumstances according to standard clinical techniques. An effective immunizing amount is that amount sufficient to treat or prevent a PPV5A infectious disease in a subject. Effective doses may also be extrapolated from dose-response curves derived from animal model test systems and can vary from 0.1 mg/kg to 20 mg/kg, preferably 1 mg/kg to 10 mg/kg.

Immunogenicity of a composition can be determined by monitoring the immune response of test subjects following immunization with the composition by use of any immunoassay known in the art. Generation of a humoral (antibody) response and/or cell-mediated immunity, may be taken as an indication of an immune response. Test subjects may include animals such as pigs, mice, hamsters, dogs, cats, rabbits, cows, horses, sheep, and poultry (e.g. chickens, ducks, geese, and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., quantitative PCR, virus isolation or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model subject at suitable time intervals before, during, or after therapy. Any change or absence of change in the amount of the molecule can be identified and correlated with the effect of the treatment on the subject. The level of the molecule can be determined by any method known in the art.

After vaccination of an animal to a PPV5A using the methods and compositions of the present invention, any binding assay known in the art can be used to assess the binding between the resulting antibody and the particular molecule. These assays may also be performed to select antibodies that exhibit a higher affinity or specificity for the particular antigen.

G. Detection and Diagnostic Methods

Antibodies, or binding portions thereof, resulting from the use of native PPV5A, attenuated virus, proteins or peptides of the present invention are useful for detecting in a sample the presence of PPV5A. This detection method comprises the steps of providing an isolated antibody or binding portion thereof raised against a native PPV5A, attenuated virus, protein or peptide of the invention, adding to the isolated antibody or binding portion thereof a sample suspected of containing a quantity of PPV5A virus and detecting the presence of a complex comprising the isolated antibody or binding portion thereof bound to PPV5A virus.

The antibodies or binding portions thereof of the present invention are also useful for detecting in a sample the presence of a PPV5A protein or peptide. This detection method comprises the steps of providing an isolated antibody or binding portion thereof raised against native PPV5A, attenuated virus, protein or peptide, adding to the isolated antibody or binding portion thereof a sample suspected of containing a quantity of the PPV5A protein or peptide, and detecting the presence of a complex comprising the isolated antibody or binding portion thereof bound to the PPV5A protein or peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a PPV5A native or attenuated virus, protein or peptide may be used to diagnose, prognose or screen for a PPV5A infection.

In another aspect, the invention provides a method of diagnosing or screening for the presence of a PPV5A infection or immunity thereto, comprising measuring in a subject the level of immunospecific binding of an antibody to a sample derived from the subject, in which the antibody immunospecifically binds a PPV5A protein or peptide in which an increase in the level of said immunospecific binding, relative to the level of said immunospecific binding in an analogous sample from a subject not having the infectious disease agent, indicates the presence of PPV5A.

Examples of suitable assays to detect the presence of PPV5A peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well known in the art.

The binding activity of a given antibody may be determined according to well known methods. Those skilled in the art will be able to determine operative and optimal assay conditions for each determination by employing routine experimentation.

An additional aspect of the present invention relates to diagnostic kits for the detection or measurement of PPV5A. Kits for diagnostic use are provided, that comprise in one or more containers an anti-PPV5A antibody, and, optionally, a labeled binding partner to the antibody. Alternatively, the anti-PPV5A antibody can be labeled (with a detectable marker, e.g., a chemiluminescent, enzymatic, fluorescent, or radioactive moiety). Accordingly, the present invention provides a diagnostic kit comprising, an anti-PPV5A antibody and a control immunoglobulin. In a specific embodiment, one of the foregoing compounds of the container can be detectably labeled. A kit can optionally further comprise, in a container, a predetermined amount of a PPV5A virus, protein or peptide recognized by the antibody of the kit, for use as a standard or control.

H. Administration to a Subject

Routes of administration include but are not limited to intranasal, oral (e.g., in drinking water), intradermal, and intramuscular. Intramuscular administration is particularly preferred. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

This application is related to U.S. Serial No.: 13/800,413, filed on Mar. 13, 2013, titled "Porcine Parvovirus 5B, Methods of Use and Vaccine" (now abandoned) and U.S. Serial No.: 14/721,490, filed on May 26, 2015 titled "Porcine Parvovirus 5B, Methods of Use and Vaccine" (now allowed), the contents of both of which are incorporated herein in its entirety.

EXAMPLES

Materials and Methods

Source of Materials:

Tissue homogenates from three pigs were received from an unusual outbreak investigation. The clinical history on the farm was of 200 lb pigs with full body muscle tremors which were present upon rest but exaggerated during movement. Following extensive testing at a veterinary diagnostic laboratory which suggested a viral agent (based on microscopic lesions) but only resulted in the identification of Agent X (a non-classical swine fever virus associated pestivirus), samples were provided to the inventors to help determine the underlying cause of the CNS signs in these animals.

DNA and Protein Analysis:

DNA analysis of samples from affected pigs was conducted using high throughput sequencing from 454 Life Sciences (Branford Conn.) ("454 technology"), performed by Operon (Huntsville Ala.). Samples were enriched for viral sequences through nuclease treatment of viral particle protect nucleic acids followed by extraction, random amplification and high throughput sequencing; performed generally as described in Victoria et. al PLoS pathogen 2008 Sep. 26; 4(9):e1000163.

Resultant sequences were initially characterized by BLASTx analysis as divergent members of the Parvoviridae family. Sequences were assembled using Sequencher software and the results of these DNA analyses coupled with targeted sequencing yielded the DNA sequence of SEQ ID NO:1, which is the putative complete coding sequence of the virus denoted as PPV5A. Further analysis of the DNA sequence using Sequencher software resulted in identification of three putative coding regions corresponding to those found in other parvovirus species, comprising the viral replicase (SEQ ID NO:2), an open reading frame "ORF3" (SEQ ID NO:3) and the viral capsid protein (SEQ ID NO:4).

Example 1: Identification of a Novel Virus

DNA sequences were identified by 454 technology (viral metagenomics) in samples of lung homogenates of two unrelated pigs from different states. BLASTn and BLASTx analysis revealed the closest identity to porcine parvovirus 4, with a maximum of 67% nucleotide identity in conserved regions of the replicase gene (REP), while the capsid (CAP) coding regions did not exhibit a discernable match at the nucleotide level. At the protein level, the putative replicase protein exhibited ~60% amino acid identity and ~50% identity in the capsid protein. The virus was denoted as a new species, porcine parvovirus 5A (PPV5A). Specific primers were developed based on the capsid coding sequence and PCR based screening of homogenates that were similar in tissue and pathological/clinical characteristics revealed presence of the agent in ~16% of samples. Based on reported clinical signs and virology data associated with the tissues screened, statistically significant association was observed with several other viral agents and clinical pathologies/histopathology.

Example 2: Identification of PPV5A as a Novel Parvovirus and Phylogentic Analysis Pair-wise amino acid identities for both the putative replicase (REP) and capsid (VP1/CAP) proteins of multiple known viral species are shown in FIG. 5. PPV5A sequence identity to PPV4, the closest relative, with both REP and CAP (~60%/50%, respectively) supporting designation of PPV5A as a new species.

Phylogenetic analysis (FIG. 6) reveals the virus to be a novel species within the Parvoviridae family and parvovirus genus, based on the conserved region of the CAP protein. Similar results are achieved using the more conserved REP protein sequence (not shown).

Example 3: Confirmation of the PPV5A as a Caustive Agent of Disease

Three PPV5a PCR positive tissue homogenates from ISU were used to inoculate cesarean-derived-colostrum-deprived (CDCD) animals in an attempt to amplify virus and determine whether co-infection with the novel parvoviruses and PRRSV resulted in increased clinical respiratory signs. In this study, there were an unexpected, high number of mortalities (20-22%) in groups inoculated with the tissue homogenate containing the novel parvoviruses and high titers of PPV5A were identified in serum using PPV5A-specific PCR targeting the capsid coding region. Tissues from one animal in this study were then used to challenge CDCD pigs to reproduce clinical signs. In this study, a systemic infection with high titers of viremia was noted in the majority of infected animals. In groups that received inocula containing PPV5A, there was a high incidence of mortality (20%), lameness, decreased average daily gain, pyrexia, and both macro- and microscopic lesions.

Example 4: Culturing, Isolation and Purification of PPV5A

Small sections of PCR positive tissues (e.g. spleen, brain, lung, intestine etc) are ground up using sterile mortar and pestle. The ground tissue is resuspended in 5-10 ml modified EMEM containing HEPES buffer and antibiotics and clarified to eliminate larger tissue masses. The supernatants are collected and serially passed through various filters to eliminate most of the larger particles including bacteria. Additionally, fecal sample suspension and serum from PCR positive animals are also being processed by serial filtration for virus isolation.

Dilutions of the filtrate are treated with trypsin or left untreated and are adsorbed onto established and primary cell cultures (listed below) in 6-well plates at specific temperatures. The inoculum is aspirated and replaced with 2 ml fresh maintenance medium. The plates are then incubated at 33-37° C. in a 5% $CO_2$ atmosphere and are observed daily for cytopathic effects such as cell rounding, cell-cell fusion, sloughing, cell clustering etc as compared to mock (plain media) inoculated controls. Potential positive wells are screened for virus growth/isolation by PCR.

Established cell lines useful in isolation of virus included: ST (swine testes), SK6 (swine kidney), BHK-21 (baby hamster kidney), VIDO R1 (fetal porcine retina), PK-15 NADC (porcine kidney), PK/WRL (porcine kidney), HRT-180 (human colorectal adenocarcinoma), Hep2 (human epithelial), Vero (African green monkey kidney) and RK-13 (rabbit kidney) among others.

Primary cell cultures useful in the process include: Embryonic porcine lung, kidney, testes, trachea, and intestine cultures, among others.

As the virus is isolated, it is purified by multiple rounds of plaque purification or limiting dilutions and amplified in larger quantities and generate stock cultures for animal experiments.

Example 5: Preparation of a Inactivated Virus and Vaccine

Inactivation is performed between about 35-39° C. and in the presence of 2 to 15 mM BEI, still more preferred in the presence of about 10 mM BEI. Inactivation is performed for at least 24 hours, up to 24 to 72 hours. An equivalent amount of an agent that neutralizes the inactivation agent within the solution is then added; e.g., sodium thiosulfate to an equivalent amount. An inactivated virus preparation is prepared in accordance with methods known in the art, e.g., as disclosed in Preuss, T., et al., Comparison of Two Different Methods for Inactivation of Viruses in Serum, CLINICAL AND DIAGNOSTIC LABORATORY IMMUNOLOGY, (1997), 504-508 or Bahnemann, H. G., Inactivation of viral antigens for vaccine preparation with particular reference to the application of binary ethylenimine, VACCINE, (1990), 299-303. Once an inactivated virus is prepared, the material is combined with a carrier preparation for final vaccine formulation.

Example 6: Preparation of an Attenuated Virus and Vaccine

An attenuated virus preparation is prepared in accordance with methods known in the art, e.g., as disclosed in Vaccine Protocols, 2nd edition; Robinson, Husdon, Cranage, eds, Humana Press 2003. For example, ". . . wild type viruses are extensively passaged in tissue culture/animal hosts until an acceptable balance is reached between loss of virulence and retention of immunogenicity . . . ."

Attenuated virus is purified by multiple rounds of plaque purification or limiting dilutions. PCR assays, deep sequencing or immunofluorescence assays are utilized to determine the specificity of the culture material.

An attenuated viral vaccine is prepared by combining a purified attenuated virus preparation with a carrier preparation.

Example 7: Preparation of a Subunit Vaccine Comprising a Capsid Protein

The capsid protein of SEQ ID NO:4 was prepared by expression of the cloned SEQ ID NO:4, or fragments thereof, in various protein expression systems.

Baculovirus Expression:

PPV5A capsid protein of SEQ ID NO:4 was expressed in a baculovirus expression system, generally in accordance with the methods disclosed in Kost et al. (6), 2012. The protein was found in low quantity within the insoluble fraction upon initial purification. Methods to increase yield and solubility include, but are not limited to, use of alternative buffer conditions (e.g. urea or guanidine hydrochloride), alternative binding and purification conditions (e.g. cobalt or nickel affinity columns, anion or cation exchange columns), or alternative expression conditions (e.g. temperature, time, alternative cell lines).

Bacterial Expression:

PPV5A capsid protein of SEQ ID NO:4 was expressed in a bacterial expression system, generally in accordance with the methods disclosed in EMD Chemicals Inc. Novagen User Protocol TB184. This method included the addition of an inherent HIS-tag contained in the bacterial vector (EMD Chemicals Inc., 2011 (7)) to facilitate purification of the produced protein. Bacterially expressed HIS-tagged capsid protein was purified generally in accordance with the methods disclosed in GE Healthcare, 2012 (8) and resultant products used to generate PPV5A specific antibodies as described in Example 8.

An attenuated subunited vaccine was prepared by combining a purified capsid protein preparation with a carrier preparation.

Example 8: Preparation of Antibodies that Specifically Bind to PPV5A

Antibodies that specifically bind to PPV5A are prepared by immunizing rabbits with antigenic preparations of PPV5A virus, or subunit protein preparations of capsid (SEQ ID NO:4) proteins or fragments thereof. Serum samples from the inoculated rabbits are screened for polyclonal antibodies which bind to the PPV5A antigens. Spleens from inoculated mice which were determined to produce antibodies to the antigen are fused with myeloma cells to produce hybridomas. The hybridomas are then screened for binding to PPV5A antigen.

Polyclonal Antibodies:

The HIS-tagged bacterially expressed capsid protein prepared in accordance with Example 7 was used to immunize two New Zealand White rabbits at a custom antibody production service (Rockland Antibodies and Assays; Gilbertsville, Pa.). Rabbits were immunized with approximately 100 μg antigen/rabbit at D0, D7, D14 and D28. For D0 and D7 inoculation, animals were inoculated intradermally; inoculations given at D14 and 28 were administered subcutaneously. Complete Freund's adjuvant was used in the first inoculation; incomplete Freud's adjuvant was used in subsequent inoculations. Serum samples from both rabbits were collected before immunization and at 38 and 45 days post immunization.

Polyclonal antibody preparations were screened for anti-PPV5A specificity by Rockland Antibodies and Assays. Antibodies were produced having binding specificity to purified or partially purified PPV5A protein by immunofluorescent assay (IFA), western blot, and enzyme-linked immunosorbent assay (ELISA). Parameters for specificity of each assay were as follows: western blot specificity were measured by detection of the predicted 88.8 kDa sized protein, IFA specificity measured by comparison to uninfected cells, and ELISA specificity by coating plate with non-relevant protein.

Monoclonal Antibodies:

HIS-tagged baculovirus expressed capsid protein prepared in accordance with Example 7 are used to generate monoclonal antibodies in Balb/c mice at a custom antibody production service (Rockland Antibodies and Assays; Gilbertsville, Pa.). Mice are immunized with various PPV5A antigenic preparations according to standard protocols designed by the custom antibody production facility. The immune response following inoculation is monitored by the custom antibody production facility and antibody candidates are selected for generation of hybridomas. Standard protocols for generation of monoclonal antibodies are well known to those in the art, e.g. as disclosed in Gabriele et al. (9), p. 117-135.

Hybridomas are generated by combining B-cell tumor cells cultivated in hybridoma medium to the proliferation phase with spleen cells harvested from inoculated mice determined to produce antibodies to PPV5A antigens according to standard protocols, as disclosed in Gabriele et al. (9), p. 117-135. After fusion and culturing the hybridomas, the hybridomas are screened for binding to PPV5A antigens, and anti-PPV5A producing hybridomas are selected. Monoclonal antibodies produced by hybridomas are purified using affinity chromatography according to standard protocols, as disclosed in Gabriele et al. (9), p. 209-232.

High affinity antibodies specific for PPV5A are identified and further characterized, including determining the epitopes to which they bind, the specificity of the antibody with respect to other related virus species, and suitable high affinity antibodies with high specificity for the PPV5A viral antigen(s) are selected, using immunological techniques well known to the art, e.g. ELISA, Westernblot analysis and epitope mapping (Epitope Mapping Protocols in Methods in Molecular Biology, Vol. 66 (Glenn E. Morris, Ed., 1996) Humana Press, Totowa, N.J.).

Example 9: Diagnostic Assays for PPV5A

ELISA Assay:

Antibodies prepared in accordance with Example 8 are used to measure PPV5A in a biological sample using ELISA procedures. The assay is conducted as follows:

Coating antigen selected from the capsid protein of SEQ ID NO:4 is diluted in coating buffer (0.05 M carbonate-bicarbonate buffer; pH 9.6) to achieve a final concentration of 8 ng/μl. Plates (High protein binding 96-well ELISA plates Phenix cat no. MPG-655061) are coated with 50 μl/well of coating antigen. Plates are sealed and incubated for 1 hr. at 37° C. or overnight at 4° C. The coating solution is removed and the plate is wash plate three times with 200 μl/well PBST (1×PBS+0.05% Tween-20). The plate is coated with 300 μl/well blocking solution (0.5% w/v non-fat dry milk in PBS), sealed and incubated for 1 hr. at 37° C. The blocking solution is removed and the plate is and washed three times with 200 μl/well PBST. Samples are diluted 1:100 in blocking solution; 100 μl/well of serum samples are added to the plate. Plates are sealed and incubated for 1 hr.

at 37° C. Serum samples are removed and the plate is washed three times with 200 μl/well PBST. The secondary antibody (HRP-conjugated-goat anti-swine IgG (H+L); Jackson Immuno-Research 114-035-003) is diluted to 1:10,000 in blocking solution and used to coat the plate with 100 μl/well. Plates are sealed and incubated for 1 hr. at 37° C. The secondary antibody is removed and the plate is washed three times with 200 μl/well PBST. Plates are coated with 50 μl/well TMB (3,5,3',5'-tetramethylbenzidine; KPL cat no. 53-00-01). Plates are incubated at room temperature in the dark for approximately ten minutes. Plates are coated with 50 μl/well stop solution (2 M $H_2SO_4$; KPL cat no. 50-85-04). The optical density is read at 450 nm.

PCR Assays:

Gel-based PCR and qPCR assays for PPV5A have been optimized. These assays are conducted as follows: For the qPCR assay, each reaction is prepared by adding the following reagents: 10 μl/reaction of 2× SsoFast probe supermix (BioRad, cat no. 172-5233), 5 μl/reaction DEPC-treated water, 1 μl/reaction of the forward primer at a 6 μM concentration (AAT GCG TGT GCT TAC GCT TA: SEQ ID NO:6), 1 μl/reaction of the reverse primer at a 6 μM concentration (TGG GTT CGA ATA TGA AGA GG: SEQ ID NO:7), 1 μl/reaction of the probe at a 4 μM concentration (6-FAM/TC ATC AGG AAC CCT GGA GTG ATC TCA/BHQ_1: SEQ ID NO:8) and 2 μl/reaction of extracted DNA. The reaction is performed on a T100 thermal cycler (Bio-Rad) for one cycle at 95° C. for 2 minutes followed by forty cycles at the following two temperatures: 95° C. for 5 seconds followed by 60° C. for 5 seconds. Data is read using a CFX96 optical imaging system (Bio-Rad). For the gel-based assay, each reaction is prepared by adding the following reagents: 12.5 μl/reaction of 2× AmpliTaq Gold Mastermix (Applied Biosystems, cat no. 4302758), 8.0 μl/reaction DEPC-treated water, 1.25 μl/reaction of the forward primer (GTA CTA TGA ATT TCC AAA CGA TCT TCC TTT CG: SEQ ID NO:9) at a 10 μM concentration, 1.25 μl/reaction of the reverse primer (TTA CAC CAA ATC TGG GAC TCT AAA CAG GC: SEQ ID NO:10) at a 10 μM concentration, and 2 μl/reaction of extracted DNA. The reaction is performed on a T100 thermal cycler (Bio-Rad) for one cycle at 95° C. for 5 minutes followed by forty cycles at the following temperatures: 95° C. for 30 seconds, 60° C. for 30 seconds and 72° C. for 45 seconds followed by a final extension at 72° C. for 10 minutes.

Example 10: Evaluation of the Efficacy of PPV5a Vaccine in Pigs

To evaluate the efficacy of the composition of matter that comprises at least one PPV5A protein or polypeptide (prototype PPV5A vaccine) in pigs, a randomized study using five week old colostrum-deprived-cesarean-derived (CDCD) animals randomized into three groups (see Table 2) is performed. Animals are vaccinated with a composition or a placebo (phosphate buffered saline; PBS) at study day 0 (D0) and D14. Animals are challenged on D28 with material known to contain PPV5A. Clinical observations, rectal temperatures, weight measurements and blood collection are monitored. At D56, animals are necropsied to evaluate macroscopic lesions. The efficacy of the PPV5A vaccine is determined by statistically comparing the percent mortality, viremia (titers and duration), seroconversion (titers and duration) and clinical signs between vaccinated and non-vaccinated animals.

TABLE 2

| Group no. | Group | N | Room | Vaccination | Challenge |
|---|---|---|---|---|---|
| 1 | PPV5A-Vx | 10 | 1 and 2 | PPV5A prototype | Yes |
| 2 | PBS-Vx | 10 | 1 and 2 | PBS | Yes |
| 3 | Strict control | 5 | 3 | None | No |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

(1) Cságola A, et al., Detection, prevalence and analysis of emerging porcine parvovirus infections. Arch Virol. June; 157(6):1003-10 (2012).
(2) Hijikata M, et al., Identification of new parvovirus DNA sequence in swine sera from Myanmar. Jpn J Infect Dis 54:244-245 (2001).
(3) Wang F, et al., Novel parvovirus sublineage in the family of Parvoviridae. Virus Genes 41:305-308 (2010).
(4) Lau S K, et al., Identification of novel porcine and bovine parvoviruses closely related to human parvovirus 4. J Gen Virol 89:1840-1848 (2008).
(5) Cheung A K, et al., Identification and molecular cloning of a novel porcine parvovirus. Arch Virol 155(5):801-806 (2010).
(6) Kost et al., Recombinant baculoviruses as mammalian cell gene-delivery vectors, Trends in Biotechnology, 20, 173-180, April 2002. cited by other.
(7) EMD Chemicals Inc. 2011. *Xa/LIC Kits, User Protocol TB*184.
(8) GE Healthcare. *Recombinant Protein Purification Handbook.* 18-1142-75.
(9) Gabriele et al. (eds.), *Antibody Methods and Protocols*, Methods in Molecular Biology, 2012, vol. 901, chapter 7.

What is claimed is:

1. A method of generating an immune response in a mammal, comprising administering an immunologically-effective amount of a killed or attenuated porcine parvovirus 5A (PPV5A); comprising:

a) a nucleic acid sequence of SEQ ID NO: 1, or b) a nucleic acid sequence 97% identical to SEQ ID NO:1, which encodes a polypeptide having immunologically-effective activity of a polypeptide of SEQ ID NO:3 or SEQ ID NO:4.

2. A method of generating an immune response in a mammal, comprising administering an immunologically-effective amount of a killed or attenuated PPV5A comprising the nucleic acid sequence of SEQ ID NO: 1, which encodes polypeptide comprising:

a) the amino acid sequence of SEQ ID NO:2, SEQ ID NO:3 or SEQ ID NO:4;

b) an amino acid sequence 80% identical to SEQ ID NO:2, SEQ ID NO:3 or SEQ ID NO:4 and having a biological or immunologically-effective activity of a polypeptide encoded by SEQ ID NO:2, SEQ ID NO:3 or SEQ ID NO:4;

c) a fragment of the amino acid sequence of SEQ ID NO:2, SEQ ID NO:3 or SEQ ID NO:4, comprising at least 15 contiguous amino acids of SEQ ID NO:2, SEQ ID NO:3 or SEQ ID NO:4;

d) a fragment of the amino acid sequence of SEQ ID NO:2, SEQ ID NO:3 or SEQ ID NO:4, comprising at least 15 contiguous amino acids of SEQ ID NO:2, SEQ ID NO:3 or SEQ ID NO:4, and having an immunologically-effective activity; or e) a protein fragment that is encoded by a polynucleotide that comprises at least 15 nucleotides included in the sequences of nucleotides 87-1967 of SEQ ID NO:1, nucleotides 1975-2844 of SEQ ID NO:1, or nucleotides 2845-5547 of SEQ ID NO:1.

3. A method of generating an immune response in a mammal, comprising administering an immunologically-effective amount of a killed or attenuated PPV5A comprising:

a) a nucleic acid sequence of SEQ ID NO:1, or b) a nucleic acid sequence 97% identical to SEQ ID NO:1, which encodes a polypeptide having immunologically-effective activity of a polypeptide of SEQ ID NO:3 or SEQ ID NO:4.

4. A method of generating an immune response in a mammal, comprising administering an immunologically-effective amount of an immunogenic composition according to claim 1.

5. A method of generating an immune response in a mammal, comprising administering an immunologically-effective amount of an immunogenic composition according to claim 2.

6. A method of generating an immune response in a mammal, comprising administering an immunologically-effective amount of an immunogenic composition according to claim 3.

7. A method of inducing an immune response against a virulent PPV5A, comprising a subunit of a killed or attenuated form of a PPV5A of claim 3.

8. A method according to claim 7, wherein the subunit is a capsid protein of SEQ ID NO:4.

9. A method according to claim 7, wherein the subunit is an immunologically-effective fragment of a polypeptide of SEQ ID NO:4.

* * * * *

SEQUENCE LISTING

```
<160> NUMBER OF SEQ ID NOS: 11

<210> SEQ ID NO 1
<211> LENGTH: 5853
<212> TYPE: DNA
<213> ORGANISM: Porcine parvovirus 5A
```

<400> SEQUENCE: 1

```
tatttgcagg cttttccctg atattgggaa gattcctggg gtgactcctg agcggtatat     60
ttatgctgta aacgtgagta cccgtaatgg gcaaaagtgg ccgaaagttg ggaccgaggg    120
gccattggct gcaggtgtct tacaggggga ggcccttttc cgtgagaccc ttaaagaggt    180
ccggaaggtg tgccggctgc cgcaagaccc cccatctttt ctttcaattg gagaaagttg    240
attccaaagg gggtcttcac cttcattttt gtattagtgt tgctgctggc actcctagag    300
atgtgtcttc gatgtttaaa gccattgagc gtcgagtttc cttttactac tttggtgtag    360
agggcttgac ttttttact cctcataaaa ataagcatgg ggcttggaag agtaatgatg    420
agggctttat tgtgaattat cttcttaaaa aattgccttt gtctgagtgt gtgtatgcgt    480
ggactaatat ggatggggtg attggcgatg cctgtctgaa tgaagataag cgcagggaat    540
tgttgtctga gcgtcaagat cagggagtca ttaaagagct cactgctcct acttttaaag    600
ctgctacggg tgataaaatg ttgagtgtgg tggattggat gtgtgataat gatgtgacta    660
cggagcgccg atgggaggaa atatcggctg cgtccctgta ctctttcctt gctaccccag    720
ctggcactca tttggctaaa cagtgtctta gagctgcgaa tcagcgtatt gtgagcacta    780
aaacctcttg gttgagtctc tgtaaatttg ccagtgaaaa ggagcttcgt gcttttcaaa    840
atggggatcc tgagttgtct tcagacaaca ataggatcta ttacttattt gctatgaata    900
attactgccc tgatatggcc agtatgattt tcttttggtg gtctatgcgc caaacgggta    960
agagaaacag tatttggctg tttggacctg ctacaaccgg taaaaccaat ttagcaagtg   1020
ctattgcaca tactgctgcc agttatgggt gtgttaactg gaataacgca aatttcccgt   1080
ttcaagacat tgtgaatgtg caactgggtt ggtgggagga aggaaagatg acagaggatg   1140
tggttgaatg tgctaaggca ttgctagggg gaagtaatgt aagagttgac cgcaaatgta   1200
tgcaatctgc ggaagtgcaa tctcctcctt ttattatcac atccaatacg gatatgtgcc   1260
ttgtttctca aggcagttac atcagttttg agcaccagca gcctctccag gatagaatga   1320
ttaaatttga gtttaaccat gttcttcctg gcaatttcgg cctcatttct gaagatgaag   1380
ttgtggcctt cttcagaaat ggtgcttata atgtgttgaa gcatgcgtac atgagaaagg   1440
cccagctttt tgctctcggt ccagcttcct tgccatataa gccccctacg ggtgaattag   1500
tgtgtataga ccaagctaag tctccttctc cctctgcttc tcgccgcagt gtgagaaatt   1560
ggatgacgtg tccccctgat cctgtccagg acgatcccgc tgaactggac gagtattttc   1620
ctccagatac tcctccagag gattgtcctt gtcctatttc tcctgtgagg gagtcttgtc   1680
cctcgccagg gccttgccct acccctcctc gcaaaaaaca acggaagagc aagcattgct   1740
ccttgtctgt ctctgcgggt aaagttcctg tggtggttgt gggtgattct gactcagtcc   1800
cccccgaaga aaaagaaaaa gaggaagttt ccgtgggggga atcccaggat ccacaactgt   1860
actgggacct aactctcagt caatccgacg ttcctgtgcc tgaagacgag agtacccagt   1920
ttcctgacga cgctgtggac gcttctgatc tcattgctga acagtagtta aggtatgagc   1980
cgttctactc aaagagatct ttggtctttg ttaagggaga gacttgaaag gtataaggat   2040
cgagttaaat attatggtat tttggtgcca gaacgtcctt ctaccttagc atcttatttt   2100
agtaaagacc cacctccaga tcctccaact gttaaatttg ataaacccta tcaggatgta   2160
gatagattct ggtttccaac agacgattat actgactggt atgtctggca tggagaggac   2220
agacctccta gatttaccga gcattccggt gttcagggtt ttaaaactag gtgtgagggg   2280
gggcttcctt taatgcccag tgatcccaaa ttttgcccca tacaaaattt ttgggatcag   2340
```

-continued

```
ttcgctaatt ttgatgaggg gtctccgtcc acccagatcg gtgagagtgt ttcatggagt   2400
gatcattttg gaagtcccga tccctctcat catcaggagg tgagggatgc tgatgaagtt   2460
acttccgagc ggcagcaata taaaaatagg attgtcacct tactaagaaa agtttattgg   2520
gctaagcagt ggtctgggaa attacaaatt aatgttcctt ccctcgaaag cctttatgag   2580
cagatcccct atatgctagc ctatatggac gccgataatt ggcgtcagaa tttgttagct   2640
gctaaaactc tgcgaaccac tttggaagca ttttcctgtg ttccagatcc ttccacgtgc   2700
gatgtcacaa tctccacacc cctatctggt gaaacggatc ccgcctcttt tgcaaaatac   2760
ttatgttccc ttgtatgcaa caggtctcaa gaaaaagaac aggcgcagac gccttctttg   2820
tctccatcta agcaaaaagg gcagatgtca agtcctgatt ctgcatcgat ctcccaacct   2880
ccccctgaaa gtcacaagga tagactgctt cctaaaactg atccccttca ggaagcaggg   2940
ccccttcccg ctccccctac agctcagaag cctattatct ctaagggtgc aggcggtgga   3000
gggtcgtctg gcttcataat ccctccaaaa cctcctagcc ccgatcatac taaagatccc   3060
ccccctcctc ctcctccctc tccaattcct cctcctacat ctgcgcctga cgcagaggag   3120
cacgagctag agcgtgctaa gcaggagaaa caagaggaag atgagctcat tgaaagaatc   3180
aaatcaggag aaggagaagg agaacgagga ggcttcgtct tgccttctca ccactacact   3240
ggtcctagaa atcctgtccc agctggcaag cctgctgacc ccgttgatga atcttctgcg   3300
agacatgaca tcaggtatgg gcaacgtctt aaacatggag actggccata cctgtggggg   3360
aaggacttgg ataatgctca gcgagatgag attatcaaag ctcttcatag tcatgtcaaa   3420
gtgggaaccc aattggcagg gaatatagtg aggagtatct ggaaggctaa ggagctctta   3480
acagaacctg tgtatgagct gttaaagtct attctccctc cttcagattt atctaaagtt   3540
cctcttcctc attcccaaca gacagacaga acagaagatc cagaaactcc aggggagact   3600
agaggaactg gatcagacag tcctcgatct cctcggcctt ctggatcaac tgaagacggg   3660
ggaggtcctt cttccgagtc cagattacct gggagtaaag ttccagtaga cccatctgcc   3720
accacgtctg aagcaaagag gcagaggact gaggagggga tggacatatc ttcatgcggt   3780
ccagggggga tttctgcttc tggggctgct tcaaataact ctggtcttgc ttgtgggggt   3840
gggggggggta ctaatttagg gacagaatct cttgtatccg gctgtcagtt tggtaaaaac   3900
tctgtgatca cttcatcttt tagacgatgt cttatttcac cctggcctga taaatactgt   3960
tgttcttctg ctcacgatct tattcccgga gtggtctacg agacccttg gtgctattat    4020
gatctgaacg tcatctcaag ctacattttt tctccttctg cttggcagag gcttttggag   4080
gattatgatg cctttcgacc taaatccctt aaagttacca tccagtcttt agttttaaag   4140
atgtctgtca aggtgcagaa aaaacaaact acagttcagg attcccagtc agccactatt   4200
gctatctttg aggataaaga ctatgactac ccctatgtga tgggaggggg tcaaaaaaca   4260
gttccgggtc acttgcccgg tcaaccttat aatcttccca agtattctta cagaaccctt   4320
ggttcagtca aagaaagtaa tagggccagt atgggcggtt cagggtacac tttcaaatcc   4380
aatcaagata cggaattgtt cctgcttgaa acacatgatg ccactcttat tcgaggcggg   4440
ggtacttttg agcagtacta tgaatttcca aacgatcttc ctttcgaaaa tttgactcag   4500
tatccttggg atatccgccg tcaggataac ccccctctatc agcagaggat cactgtcatg   4560
tcaggttctg acagagatac ggtaggcatt ctagatggag atttttactc tccttttcgg   4620
ttcaaaggac atgatagacc cgccatgtgg ctgccaggac agaggttgat tcagggcaaa   4680
ttcatagata cgcacccaat acccaataca gggaggagtg ggttcatcc taatgatttt    4740
```

-continued

```
cacacaaggg gcgatggtca tggtgacacc catagaacac atgaagagag gatctacagt   4800

ctagatacag gtcttgctgc tatgccacgt gccgctcata gacccaccct tcagcccgga   4860

cctaggactc tgtctcatgc cgtacgcaga cccgatggtt ccaccgtggt cacggctaat   4920

gcgtgtgctt acgcttacac ccaggagaat cctcatcagg aaccctggag tgatctcaat   4980

gtcagacata ccatgtatag gttagcctat caacgtcaaa aaggttttca gcaacccggg   5040

gaccctcttc atattcgaac ccatgcttgt tatggggacg gggatgttac cattccaaaa   5100

gaagagtcct tatggcctac tgttctgggt agttgcacag aaaagtcccc tgcctgttta   5160

gagtcccaga tttggtgtaa aacaccaaat gtggacatgg tctatggaga acacacaccc   5220

cctcttgctt tatggggtat gcatgctccc ccaccccatg tatttctcag gatgcttgct   5280

caagagggtc ctcctaatgt cagtacttgc agaccggctc aatctggtca gaccttcatc   5340

aatcaatatg gtcagtttct cctctgtttt accatggtat gggaagttaa gcctagaccc   5400

aagtccatca agcagtggaa tccacgtccg cccatcagca ttcctgttgg tcagtctggt   5460

cctgctttca ttctcgatca agatggctac taccgtctcc cagaacatgt ctggtctgcc   5520

agggaacgta tccgcagcaa acgctagtgc ccccagcaat acacttacta cagtattgat   5580

gtgtcaggca ttctggttga ttgtttttatt ttggctccgc ctactgtatg gcccatgtaa   5640

acgcatctat tatgaaaata aaatacgtca attgctgatg taattcgtgt tgtaattctt   5700

gttttgaaaa gcgcatattt tcttgccggt ctgagtaaca ccacctatga catcatataa   5760

atttgattac gtaacttcct ctttttactt ccgtcttttt ttgattacgc aatatacaca   5820

attctagcag ttaactatta cacaatatca cac                                5853
```

```
<210> SEQ ID NO 2
<211> LENGTH: 626
<212> TYPE: PRT
<213> ORGANISM: Porcine parvovirus 5A

<400> SEQUENCE: 2

Met Gly Lys Ser Gly Arg Lys Leu Gly Pro Arg Gly His Trp Leu Gln
1               5                   10                  15

Val Ser Tyr Arg Gly Arg Pro Phe Ser Val Arg Pro Leu Lys Arg Ser
            20                  25                  30

Gly Arg Cys Ala Gly Cys Arg Lys Thr Pro His Leu Phe Phe Gln Leu
        35                  40                  45

Glu Lys Val Asp Ser Lys Gly Gly Leu His Leu His Phe Cys Ile Ser
    50                  55                  60

Val Ala Ala Gly Thr Pro Arg Asp Val Ser Ser Met Phe Lys Ala Ile
65                  70                  75                  80

Glu Arg Arg Val Ser Phe Tyr Tyr Phe Gly Val Glu Gly Leu Thr Phe
                85                  90                  95

Phe Thr Pro His Lys Asn Lys His Gly Ala Trp Lys Ser Asn Asp Glu
            100                 105                 110

Gly Phe Ile Val Asn Tyr Leu Leu Lys Lys Leu Pro Leu Ser Glu Cys
        115                 120                 125

Val Tyr Ala Trp Thr Asn Met Asp Gly Val Ile Gly Asp Ala Cys Leu
    130                 135                 140

Asn Glu Asp Lys Arg Arg Glu Leu Leu Ser Glu Arg Gln Asp Gln Gly
145                 150                 155                 160

Val Ile Lys Glu Leu Thr Ala Pro Thr Phe Lys Ala Ala Thr Gly Asp
                165                 170                 175
```

```
Lys Met Leu Ser Val Val Asp Trp Met Cys Asp Asn Asp Val Thr Thr
            180                 185                 190

Glu Arg Arg Trp Glu Glu Ile Ser Ala Ala Ser Leu Tyr Ser Phe Leu
        195                 200                 205

Ala Thr Pro Ala Gly Thr His Leu Ala Lys Gln Cys Leu Arg Ala Ala
    210                 215                 220

Asn Gln Arg Ile Val Ser Thr Lys Thr Ser Trp Leu Ser Leu Cys Lys
225                 230                 235                 240

Phe Ala Ser Glu Lys Glu Leu Arg Ala Phe Gln Asn Gly Asp Pro Glu
                245                 250                 255

Leu Ser Ser Asp Asn Asn Arg Ile Tyr Tyr Leu Phe Ala Met Asn Asn
            260                 265                 270

Tyr Cys Pro Asp Met Ala Ser Met Ile Phe Phe Trp Trp Ser Met Arg
        275                 280                 285

Gln Thr Gly Lys Arg Asn Ser Ile Trp Leu Phe Gly Pro Ala Thr Thr
    290                 295                 300

Gly Lys Thr Asn Leu Ala Ser Ala Ile Ala His Thr Ala Ala Ser Tyr
305                 310                 315                 320

Gly Cys Val Asn Trp Asn Asn Ala Asn Phe Pro Phe Gln Asp Ile Val
                325                 330                 335

Asn Val Gln Leu Gly Trp Trp Glu Glu Gly Lys Met Thr Glu Asp Val
            340                 345                 350

Val Glu Cys Ala Lys Ala Leu Leu Gly Gly Ser Asn Val Arg Val Asp
        355                 360                 365

Arg Lys Cys Met Gln Ser Ala Glu Val Gln Ser Pro Pro Phe Ile Ile
    370                 375                 380

Thr Ser Asn Thr Asp Met Cys Leu Val Ser Gln Gly Ser Tyr Ile Ser
385                 390                 395                 400

Phe Glu His Gln Gln Pro Leu Gln Asp Arg Met Ile Lys Phe Glu Phe
                405                 410                 415

Asn His Val Leu Pro Gly Asn Phe Gly Leu Ile Ser Glu Asp Glu Val
            420                 425                 430

Val Ala Phe Phe Arg Asn Gly Ala Tyr Asn Val Leu Lys His Ala Tyr
        435                 440                 445

Met Arg Lys Ala Gln Leu Phe Ala Leu Gly Pro Ala Ser Leu Pro Tyr
    450                 455                 460

Lys Pro Pro Thr Gly Glu Leu Val Cys Ile Asp Gln Ala Lys Ser Pro
465                 470                 475                 480

Ser Pro Ser Ala Ser Arg Arg Ser Val Arg Asn Trp Met Thr Cys Pro
                485                 490                 495

Pro Asp Pro Val Gln Asp Asp Pro Ala Glu Leu Asp Glu Tyr Phe Pro
            500                 505                 510

Pro Asp Thr Pro Pro Glu Asp Cys Pro Cys Pro Ile Ser Pro Val Arg
        515                 520                 525

Glu Ser Cys Pro Ser Pro Gly Pro Cys Pro Thr Pro Pro Arg Lys Lys
    530                 535                 540

Gln Arg Lys Ser Lys His Cys Ser Leu Ser Val Ser Ala Gly Lys Val
545                 550                 555                 560

Pro Val Val Val Val Gly Asp Ser Asp Ser Val Pro Pro Glu Glu Lys
                565                 570                 575

Glu Lys Glu Glu Val Ser Val Gly Glu Ser Gln Asp Pro Gln Leu Tyr
            580                 585                 590
```

```
Trp Asp Leu Thr Leu Ser Gln Ser Asp Val Pro Val Pro Glu Asp Glu
        595                 600                 605

Ser Thr Gln Phe Pro Asp Asp Ala Val Asp Ala Ser Asp Leu Ile Ala
    610                 615                 620

Glu Gln
625


<210> SEQ ID NO 3
<211> LENGTH: 290
<212> TYPE: PRT
<213> ORGANISM: Porcine parvovirus 5A

<400> SEQUENCE: 3

Met Ser Arg Ser Thr Gln Arg Asp Leu Trp Ser Leu Leu Arg Glu Arg
1               5                   10                  15

Leu Glu Arg Tyr Lys Asp Arg Val Lys Tyr Tyr Gly Ile Leu Val Pro
            20                  25                  30

Glu Arg Pro Ser Thr Leu Ala Ser Tyr Phe Ser Lys Asp Pro Pro Pro
        35                  40                  45

Asp Pro Pro Thr Val Lys Phe Asp Lys Pro Tyr Gln Asp Val Asp Arg
    50                  55                  60

Phe Trp Phe Pro Thr Asp Asp Tyr Thr Asp Trp Tyr Val Trp His Gly
65                  70                  75                  80

Glu Asp Arg Pro Pro Arg Phe Thr Glu His Ser Gly Val Gln Gly Phe
                85                  90                  95

Lys Thr Arg Cys Glu Gly Gly Leu Pro Leu Met Pro Ser Asp Pro Lys
            100                 105                 110

Phe Cys Pro Ile Gln Asn Phe Trp Asp Gln Phe Ala Asn Phe Asp Glu
        115                 120                 125

Gly Ser Pro Ser Thr Gln Ile Gly Glu Ser Val Ser Trp Ser Asp His
    130                 135                 140

Phe Gly Ser Pro Asp Pro Ser His His Gln Glu Val Arg Asp Ala Asp
145                 150                 155                 160

Glu Val Thr Ser Glu Arg Gln Gln Tyr Lys Asn Arg Ile Val Thr Leu
                165                 170                 175

Leu Arg Lys Val Tyr Trp Ala Lys Gln Trp Ser Gly Lys Leu Gln Ile
            180                 185                 190

Asn Val Pro Ser Leu Glu Ser Leu Tyr Glu Gln Ile Pro Tyr Met Leu
        195                 200                 205

Ala Tyr Met Asp Ala Asp Asn Trp Arg Gln Asn Leu Leu Ala Ala Lys
    210                 215                 220

Thr Leu Arg Thr Thr Leu Glu Ala Phe Ser Cys Val Pro Asp Pro Ser
225                 230                 235                 240

Thr Cys Asp Val Thr Ile Ser Thr Pro Leu Ser Gly Glu Thr Asp Pro
                245                 250                 255

Ala Ser Phe Ala Lys Tyr Leu Cys Ser Leu Val Cys Asn Arg Ser Gln
            260                 265                 270

Glu Lys Glu Gln Ala Gln Thr Pro Ser Leu Ser Pro Ser Lys Gln Lys
        275                 280                 285

Gly Gln
    290


<210> SEQ ID NO 4
<211> LENGTH: 792
<212> TYPE: PRT
<213> ORGANISM: Porcine parvovirus 5A
```

-continued

```
<400> SEQUENCE: 4

Met Gln Arg Ile Asn Ser Gly Glu Gly Glu Gly Glu Arg Gly Gly Phe
1               5                   10                  15

Val Leu Pro Ser His His Tyr Thr Gly Pro Arg Asn Pro Val Pro Ala
            20                  25                  30

Gly Lys Pro Ala Asp Pro Val Asp Glu Ser Ser Ala Arg His Asp Ile
        35                  40                  45

Arg Tyr Gly Gln Arg Leu Lys His Gly Asp Trp Pro Tyr Leu Trp Gly
    50                  55                  60

Lys Asp Leu Asp Asn Ala Gln Arg Asp Glu Ile Ile Lys Ala Leu His
65                  70                  75                  80

Ser His Val Lys Val Gly Thr Gln Leu Ala Gly Asn Ile Val Arg Ser
                85                  90                  95

Ile Trp Lys Ala Lys Glu Leu Leu Thr Glu Pro Val Tyr Glu Leu Leu
            100                 105                 110

Lys Ser Ile Leu Pro Pro Ser Asp Leu Ser Lys Val Pro Leu Pro His
        115                 120                 125

Ser Gln Gln Thr Asp Arg Thr Glu Asp Pro Glu Thr Pro Gly Glu Thr
    130                 135                 140

Arg Gly Thr Gly Ser Asp Ser Pro Arg Ser Pro Arg Pro Ser Gly Ser
145                 150                 155                 160

Thr Glu Asp Gly Gly Gly Pro Ser Ser Glu Ser Arg Leu Pro Gly Ser
                165                 170                 175

Lys Val Pro Val Asp Pro Ser Ala Thr Thr Ser Glu Ala Lys Arg Gln
            180                 185                 190

Arg Thr Glu Glu Gly Met Asp Ile Ser Ser Cys Gly Pro Gly Gly Ile
        195                 200                 205

Ser Ala Ser Gly Ala Ala Ser Asn Asn Ser Gly Leu Ala Cys Gly Gly
    210                 215                 220

Gly Gly Gly Thr Asn Leu Gly Thr Glu Ser Leu Val Ser Gly Cys Gln
225                 230                 235                 240

Phe Gly Lys Asn Ser Val Ile Thr Ser Ser Phe Arg Arg Cys Leu Ile
                245                 250                 255

Ser Pro Trp Pro Asp Lys Tyr Cys Cys Ser Ser Ala His Asp Leu Ile
            260                 265                 270

Pro Gly Val Val Tyr Glu Thr Pro Trp Cys Tyr Tyr Asp Leu Asn Val
        275                 280                 285

Ile Ser Ser Tyr Ile Phe Ser Pro Ser Ala Trp Gln Arg Leu Leu Glu
    290                 295                 300

Asp Tyr Asp Ala Phe Arg Pro Lys Ser Leu Lys Val Thr Ile Gln Ser
305                 310                 315                 320

Leu Val Leu Lys Met Ser Val Lys Val Gln Lys Lys Gln Thr Thr Val
                325                 330                 335

Gln Asp Ser Gln Ser Ala Thr Ile Ala Ile Phe Glu Asp Lys Asp Tyr
            340                 345                 350

Asp Tyr Pro Tyr Val Met Gly Gly Gly Gln Lys Thr Val Pro Gly His
        355                 360                 365

Leu Pro Gly Gln Pro Tyr Asn Leu Pro Lys Tyr Ser Tyr Arg Thr Leu
    370                 375                 380

Gly Ser Val Lys Glu Ser Asn Arg Ala Ser Met Gly Gly Ser Gly Tyr
385                 390                 395                 400

Thr Phe Lys Ser Asn Gln Asp Thr Glu Leu Phe Leu Leu Glu Thr His
                405                 410                 415
```

```
Asp Ala Thr Leu Ile Arg Gly Gly Gly Thr Phe Glu Gln Tyr Tyr Glu
            420                 425                 430

Phe Pro Asn Asp Leu Pro Phe Glu Asn Leu Thr Gln Tyr Pro Trp Asp
        435                 440                 445

Ile Arg Arg Gln Asp Asn Pro Leu Tyr Gln Gln Arg Ile Thr Val Met
    450                 455                 460

Ser Gly Ser Asp Arg Asp Thr Val Gly Ile Leu Asp Gly Asp Phe Tyr
465                 470                 475                 480

Ser Pro Phe Arg Phe Lys Gly His Asp Arg Pro Ala Met Trp Leu Pro
                485                 490                 495

Gly Gln Arg Leu Ile Gln Gly Lys Phe Ile Asp Thr His Pro Ile Pro
            500                 505                 510

Asn Thr Gly Arg Ser Gly Val His Pro Asn Asp Phe His Thr Arg Gly
        515                 520                 525

Asp Gly His Gly Asp Thr His Arg Thr His Glu Glu Arg Ile Tyr Ser
    530                 535                 540

Leu Asp Thr Gly Leu Ala Ala Met Pro Arg Ala Ala His Arg Pro Thr
545                 550                 555                 560

Leu Gln Pro Gly Pro Arg Thr Leu Ser His Ala Val Arg Arg Pro Asp
                565                 570                 575

Gly Ser Thr Val Val Thr Ala Asn Ala Cys Ala Tyr Ala Tyr Thr Gln
            580                 585                 590

Glu Asn Pro His Gln Glu Pro Trp Ser Asp Leu Asn Val Arg His Thr
        595                 600                 605

Met Tyr Arg Leu Ala Tyr Gln Arg Gln Lys Gly Phe Gln Gln Pro Gly
    610                 615                 620

Asp Pro Leu His Ile Arg Thr His Ala Cys Tyr Gly Asp Gly Asp Val
625                 630                 635                 640

Thr Ile Pro Lys Glu Glu Ser Leu Trp Pro Thr Val Leu Gly Ser Cys
                645                 650                 655

Thr Glu Lys Ser Pro Ala Cys Leu Glu Ser Gln Ile Trp Cys Lys Thr
            660                 665                 670

Pro Asn Val Asp Met Val Tyr Gly Glu His Thr Pro Pro Leu Ala Leu
        675                 680                 685

Trp Gly Met His Ala Pro Pro Pro His Val Phe Leu Arg Met Leu Ala
    690                 695                 700

Gln Glu Gly Pro Pro Asn Val Ser Thr Cys Arg Pro Ala Gln Ser Gly
705                 710                 715                 720

Gln Thr Phe Ile Asn Gln Tyr Gly Gln Phe Leu Leu Cys Phe Thr Met
                725                 730                 735

Val Trp Glu Val Lys Pro Arg Pro Lys Ser Ile Lys Gln Trp Asn Pro
            740                 745                 750

Arg Pro Pro Ile Ser Ile Pro Val Gly Gln Ser Gly Pro Ala Phe Ile
        755                 760                 765

Leu Asp Gln Asp Gly Tyr Tyr Arg Leu Pro Glu His Val Trp Ser Ala
    770                 775                 780

Arg Glu Arg Ile Arg Ser Lys Arg
785                 790
```

<210> SEQ ID NO 5
<211> LENGTH: 726
<212> TYPE: PRT
<213> ORGANISM: Porcine parvovirus 4

-continued

<400> SEQUENCE: 5

Lys His Gly His Trp Pro His Leu Trp Ala Pro Phe Val Asp Arg Gln
1 5 10 15

Met Ser Gln Glu Ile Gln Gln Val Leu Lys Gly Ser Thr Lys Leu Ser
20 25 30

Gln Lys Leu Leu Ala Asn Phe Ile Ile Ala Leu Trp Arg Ala Lys Glu
35 40 45

Lys Ile Gly Ala Pro Ile Tyr Glu Ile Val Lys Gly Val Phe Pro Ser
50 55 60

Val Asp Lys Lys Thr Val Glu Ser Leu Leu Pro His Pro Asp Pro Ile
65 70 75 80

Pro Ala Pro Pro Ser Ser Pro Gln Arg Gly Ser Lys Arg Ala Ser Pro
85 90 95

Pro Gln Ser Pro Asn Ala His Asp Glu Asp Thr Met Ser Gly His Lys
100 105 110

Arg Gln Lys Thr Met Glu Val Glu Ser Glu Cys Asp Lys Ser Leu Leu
115 120 125

Cys Pro Thr Gln Asn Ala Gly Ala Asp Phe Glu Leu Cys Gly Thr Gly
130 135 140

Gly Gly Ala Thr Asn Glu Lys Gly Thr Trp Val Gly Gly Thr Gln Phe
145 150 155 160

Thr Asp Thr Ser Ile Arg Thr Phe Gly Thr Arg Arg Cys Val Leu Ser
165 170 175

Ala Phe Pro Asp Thr Tyr Cys Ser Met Met Ser Gly Asp Ala Ile Pro
180 185 190

Ser Ile Ile Phe Asn Thr Pro Trp Tyr Tyr Tyr Asp Leu Asn Ile Met
195 200 205

Ser Cys His Phe Ser Pro Ser Ala Phe Gln Thr Leu Ile Glu Asp Tyr
210 215 220

Asp Ala Phe Arg Pro Arg Ser Leu Thr Val His Leu Lys Glu Leu Val
225 230 235 240

Ile Lys Asp Val Cys Gln Gln Gln Gly Leu Gln Ala Glu Gln Val Ser
245 250 255

Asp Asn Asn Ser Ala Thr Leu Leu Ala Phe Glu Asp Val Asn Tyr Glu
260 265 270

Leu Pro Tyr Val Leu Gly Gly Gly Gln Val Ser Val Pro Gly His Leu
275 280 285

Pro Gly Gln Pro Tyr Gln Leu Pro Lys Tyr Ser Tyr Arg Thr Val Gly
290 295 300

Lys Pro Asp Pro Asn Ser Gly Phe Val Pro Gly Arg Asn Thr His Pro
305 310 315 320

Asp Gln Gly Pro Gly His Pro Lys Ala Ser Lys Thr Ile Trp Tyr Ser
325 330 335

Gln Tyr Leu Glu Thr Gln Asp Thr Glu Phe Tyr Ile Leu Glu Asn His
340 345 350

Lys Ala Thr Ile Leu His Ser Gly Asn Thr Phe Ser Gln His Tyr Asn
355 360 365

Phe Pro Asp Leu Pro Phe Glu Gln Leu Thr Gln Tyr Met Trp Asp Ala
370 375 380

Arg Arg Gln Asp Asn Pro Leu Ile Asp Gln Arg Ile Gln Val Met Ser
385 390 395 400

Arg Met Tyr Asp Asp Gly Pro Gln Lys Thr Phe Ala Ile Lys Val Asn
405 410 415

-continued

```
Pro Tyr Ile Val Pro Phe Thr Val Lys Ser Thr Ser Arg Pro Ala Met
            420                 425                 430

Phe Leu Ala Gly Gly Arg Phe Lys Asp Gly Asp Tyr Ser Ile Thr Gly
        435                 440                 445

Pro Gly Asp Arg Asp Lys Thr Ser Phe Lys Tyr Tyr Asn Asp Pro Pro
    450                 455                 460

Trp Ile Ile Thr Arg Asp Thr Tyr Leu Phe Ser Ser Asp Leu Ala Lys
465                 470                 475                 480

Thr Glu Arg Glu Gln Pro Gly Pro Arg Gln Gly Asp Thr Val Val Arg
                485                 490                 495

Thr Pro Asp Gly Thr Leu Ile Val Thr Thr Asn Ala Leu Ala Tyr Gly
            500                 505                 510

Tyr Thr Thr Glu Tyr Leu Lys Asn Ile Pro Leu Leu Ser Ser Lys Tyr
        515                 520                 525

His Gly Val Glu Asn Phe Arg Leu Ala Val Glu Asn Glu Arg Gly Tyr
    530                 535                 540

Ser Met Pro Gly His Pro Ser His Ile Arg Glu Thr Leu Phe Arg Gly
545                 550                 555                 560

Lys Leu Pro Ser Glu Ile Arg Glu Ser Thr Ile Lys Ser Glu Asp Gln
                565                 570                 575

Arg Lys Glu Ile Thr Phe Pro Asp Tyr Met Gly Ser Val Asn Glu Lys
            580                 585                 590

Thr Thr Ala Asn Leu Glu Ser Gln Ile Trp Ser Gln Ile Pro Asn Thr
        595                 600                 605

Asp Ile Thr Glu Lys Cys Thr Thr Pro Pro Leu Ser Ile Trp Gly Met
    610                 615                 620

Lys Asn Pro Pro Pro Met Val Phe Leu Arg Leu Leu Ala Gln Met Gly
625                 630                 635                 640

Pro Pro Arg Arg Ser Ala Cys Ser Gly Ser Ile Pro Ser Asn Thr Tyr
                645                 650                 655

Leu Asn Gln Tyr Cys Gln Phe Leu Leu Thr Tyr Glu Met Glu Trp Asp
            660                 665                 670

Val Ile Lys Arg Thr Arg Lys Thr Val Arg Trp Asn Pro Ile Pro Pro
        675                 680                 685

Pro Gln Ile Pro Met Gly Pro Asn Asn Leu Pro Val Tyr Ile Leu Asn
    690                 695                 700

Lys Glu Gly Gln Tyr Arg Met Pro Thr Glu Val Trp Thr Ala Lys Gln
705                 710                 715                 720

Arg Pro Arg His Arg Arg
                725


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

aatgcgtgtg cttacgctta                                                  20


<210> SEQ ID NO 7
<211> LENGTH: 20
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 7
tgggttcgaa tatgaagagg 20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
tcatcaggaa ccctggagtg atctca 26

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
gtactatgaa tttccaaacg atcttccttt cg 32

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
ttacaccaaa tctgggactc taaacaggc 29

<210> SEQ ID NO 11
<211> LENGTH: 495
<212> TYPE: PRT
<213> ORGANISM: Porcine parvovirus 4

<400> SEQUENCE: 11

```
Leu Val Ile Ala Val Arg Gln Ala Glu Ala Leu Phe Arg Glu Leu Gln
1               5                   10                  15

Lys Glu Leu Arg Lys Ser Cys Arg Leu Gly Val Asp Pro Gly Ile Phe
            20                  25                  30

Met Gln Leu Glu Glu Val Asp Ser Lys Gly Gly Leu His Leu His Trp
        35                  40                  45

Cys Val Ser Val Ser Ala Gly Thr Pro Arg Asp Val Leu Thr Ile Phe
    50                  55                  60

Lys Asn Thr Glu Lys Lys Val Ser Gln Tyr Tyr Phe Gly Val Glu Gly
65                  70                  75                  80

Leu Ser Phe Phe Val Pro His Lys Asn Lys His Gly Ala Trp Lys Ser
                85                  90                  95

Thr Asp Glu Gly Phe Ile Tyr Asn Tyr Leu Leu Lys Lys Leu Pro Leu
            100                 105                 110

Lys Glu Cys Leu Tyr Ala Trp Thr Thr Ile Gly Gly Ala Ile Gly Asp
        115                 120                 125
```

-continued

```
Ala Cys Leu Asn Thr Asp Lys Arg Lys Glu Leu Leu Asp Asn Arg Gln
    130                 135                 140

Asp Pro Ala Val Ile Glu Glu Leu Ser Ala Pro Met Tyr Lys Cys Ala
145                 150                 155                 160

Thr Gly Glu Lys Met Leu Asp Ile Val Gln Trp Leu Val Asp Asn Asn
                165                 170                 175

Ile Cys Ser Glu Ser Arg Trp Glu Asn Lys Asn Ala Leu Ser Leu Tyr
            180                 185                 190

Ser Phe Leu Ala Thr Gln Ala Gly Gly Tyr Met Ala Lys Gln Cys Leu
        195                 200                 205

Arg Ile Ala Gln Gln Lys Leu Leu Lys Glu Lys Pro Leu Gly Leu Thr
    210                 215                 220

Leu Met Asp Phe Lys Gly Met Asn Ala Leu Arg Arg Phe Gln Gln Asp
225                 230                 235                 240

Glu Gly Glu Met Thr Phe Asp Asn Asn Arg Met His Tyr Ile Phe Ala
                245                 250                 255

Ile Asn Asn Tyr Asp Pro Lys Ile Ala Ser Val Ile Met Tyr Phe Trp
            260                 265                 270

Ser Met Lys Gln Thr Gly Lys Arg Asn Cys Val Trp Phe Tyr Gly Pro
        275                 280                 285

Ala Thr Thr Gly Lys Thr Asn Met Ala Gln Ala Ile Cys His Ser Ser
    290                 295                 300

Ala Asn Tyr Gly Asn Val Asn Trp Asn Asn Ala Asn Phe Pro Phe Gln
305                 310                 315                 320

Asp Ile Val Gly Ala Gln Val Gly Trp Trp Glu Glu Gly Lys Met Thr
                325                 330                 335

Gly Asp Met Val Glu Ala Ala Lys Ala Leu Leu Gly Gly Thr Ala Leu
            340                 345                 350

Arg Ile Asp Arg Lys Cys Met Gln Ser Ile Glu Val Asn Ser Pro Pro
        355                 360                 365

Phe Leu Ile Thr Ser Asn Val Asp Met Thr Ile Val Gln Glu Gly Ser
    370                 375                 380

Phe Val Ser Phe Glu His Gln Gln Pro Leu Glu Asp Arg Met Ile Lys
385                 390                 395                 400

Phe Ser Phe Asn Met Thr Leu Pro Gly Asn Phe Gly Leu Ile Thr Ser
                405                 410                 415

Glu Glu Val Lys Ser Phe Phe Arg Met Gly Ala Lys Leu Ala Ala Gln
            420                 425                 430

Pro Asp Ile Met Asn Cys Pro Ile Phe Lys Lys Gly Pro Ala Ser Ile
        435                 440                 445

Arg His Leu Val Pro Val Gly Glu Ile Pro Pro Pro Lys Glu Met Lys
    450                 455                 460

His Lys Arg Gln Pro Leu Tyr Met Arg Ala Glu Pro Asp Glu Ile Gln
465                 470                 475                 480

Asp Asn Pro Glu Glu Leu Asp His Trp Phe Glu Glu Glu Ala Pro
                485                 490                 495
```